US006960163B2

United States Patent
Ewers et al.

(10) Patent No.: US 6,960,163 B2
(45) Date of Patent: *Nov. 1, 2005

(54) SHAPE LOCKABLE APPARATUS AND METHOD FOR ADVANCING AN INSTRUMENT THROUGH UNSUPPORTED ANATOMY

(75) Inventors: Richard C. Ewers, Fullerton, CA (US); Vahid Saadat, Saratoga, CA (US)

(73) Assignee: USGI Medical Inc., San Clemente, CA (US)

( * ) Notice: Subject to any disclaimer, the term of this patent is extended or adjusted under 35 U.S.C. 154(b) by 341 days.

This patent is subject to a terminal disclaimer.

(21) Appl. No.: 10/281,462

(22) Filed: Oct. 25, 2002

(65) Prior Publication Data

US 2003/0233066 A1 Dec. 18, 2003

Related U.S. Application Data

(63) Continuation-in-part of application No. 10/173,203, filed on Jun. 13, 2002, and a continuation-in-part of application No. 10/173,227, filed on Jun. 13, 2002, now Pat. No. 6,790,173, and a continuation-in-part of application No. 10/173,238, filed on Jun. 13, 2002, now Pat. No. 6,837,847, and a continuation-in-part of application No. 10/173,220, filed on Jun. 13, 2002, now Pat. No. 6,783,491.

(51) Int. Cl.[7] .............................................. A61B 1/00
(52) U.S. Cl. ....................................... 600/114; 600/121
(58) Field of Search .............................. 600/114, 115, 600/117, 118, 121, 127, 129, 139–144, 146, 150, 151

(56) References Cited

U.S. PATENT DOCUMENTS 616,672 A 12/1898 Kelling

| 2,510,198 A | 6/1950 | Tesmer |
| 2,533,494 A | 12/1950 | Mitchell, Jr. |
| 3,060,972 A | 10/1962 | Sheldon |
| 3,096,962 A | 7/1963 | Meijs |

(Continued)

FOREIGN PATENT DOCUMENTS

| DE | 28 23 025 | 12/1979 |
| EP | 0 497 781 B1 | 8/1992 |

(Continued)

OTHER PUBLICATIONS

"Science & Technology," *Laptop Magazine*: p. 98 (Oct. 2002).

*Primary Examiner*—Beverly M. Flanagan
(74) *Attorney, Agent, or Firm*—Townsend and Townsend and Crew LLP

(57) ABSTRACT

Apparatus and methods are provided for placing and advancing a diagnostic or therapeutic instrument in a hollow body organ of a tortuous or unsupported anatomy, comprising a handle, an overtube disposed within a hydrophilic sheath, and a distal region having an atraumatic tip. The overtube may be removable from the handle, and have a longitudinal axis disposed at an angle relative to the handle. The sheath may be disposable to permit reuse of the overtube. Fail-safe tensioning mechanisms may be provided to selectively stiffen the overtube to reduce distension of the organ caused by advancement of the diagnostic or therapeutic instrument. The fail-safe tensioning mechanisms reduce the risk of reconfiguration of the overtube in the event that the tension system fails, and, in one embodiment, rigidizes the overtube without substantial proximal movement of the distal region. The distal region permits passive steering of the overtube caused by deflection of the diagnostic or therapeutic instrument, while the atraumatic tip prevents the wall of the organ from becoming caught or pinched during manipulation of the diagnostic or therapeutic instrument.

51 Claims, 29 Drawing Sheets

U.S. PATENT DOCUMENTS

| | | | |
|---|---|---|---|
| 3,162,214 A | 12/1964 | Bazinet, Jr. | |
| 3,168,274 A | 2/1965 | Street | |
| 3,430,662 A | 3/1969 | Guarnaschelli | |
| 3,546,961 A | 12/1970 | Marton | |
| 3,858,578 A | 1/1975 | Milo | |
| 3,913,565 A | 10/1975 | Kawahara | |
| 4,054,128 A | 10/1977 | Seufert et al. | |
| 4,176,662 A | 12/1979 | Frazer | |
| 4,366,810 A | 1/1983 | Slanetz, Jr. | |
| 4,601,283 A | 7/1986 | Chikama | |
| 4,646,722 A | 3/1987 | Silverstein et al. | |
| 4,648,733 A | 3/1987 | Merkt | |
| 4,655,257 A | 4/1987 | Iwashita | |
| 4,815,450 A | 3/1989 | Patel | |
| 4,949,927 A | 8/1990 | Madocks et al. | |
| 5,092,901 A | 3/1992 | Hunter et al. | |
| 5,174,276 A | 12/1992 | Crockard | |
| 5,217,001 A | 6/1993 | Nakao et al. | |
| 5,251,611 A | 10/1993 | Zehel et al. | |
| 5,337,732 A | 8/1994 | Grundfest et al. | |
| 5,337,733 A | 8/1994 | Bauerfeind et al. | |
| 5,348,259 A | 9/1994 | Blanco et al. | |
| 5,389,222 A | 2/1995 | Shahinpoor | |
| 5,558,665 A | 9/1996 | Kieturakis | |
| 5,624,381 A | 4/1997 | Kieturakis | |
| 5,662,587 A | 9/1997 | Grundfest et al. | |
| 5,749,828 A | 5/1998 | Solomon et al. | |
| 5,759,151 A | 6/1998 | Sturges | |
| 5,779,624 A | 7/1998 | Chang | |
| 5,897,417 A | 4/1999 | Grey | |
| 5,902,254 A | 5/1999 | Magram | |
| 5,916,147 A | 6/1999 | Boury | |
| 5,921,915 A | 7/1999 | Azonian et al. | |
| 6,042,155 A | 3/2000 | Lockwood | |
| 6,179,776 B1 | 1/2001 | Adams et al. | |
| 6,249,076 B1 | 6/2001 | Madden et al. | |
| 6,306,081 B1 | 10/2001 | Ishikawa et al. | |
| 6,315,714 B1 | 11/2001 | Akiba | |
| 6,554,793 B1 | 4/2003 | Pauker et al. | |
| 6,761,685 B2 | 7/2004 | Adams et al. | |
| 6,800,056 B2 | 10/2004 | Tartaglia et al. | |
| 2001/0000040 A1 | 3/2001 | Adams et al. | |
| 2002/0022765 A1 | 2/2002 | Belson | |
| 2002/0062062 A1 | 5/2002 | Belson et al. | |
| 2002/0120178 A1 | 8/2002 | Tartaglia et al. | |
| 2002/0147385 A1 | 10/2002 | Butler et al. | |
| 2002/0161281 A1 | 10/2002 | Jaffe et al. | |
| 2002/0193661 A1 | 12/2002 | Belson | |
| 2002/0193662 A1 | 12/2002 | Belson | |
| 2003/0045778 A1 | 3/2003 | Ohline et al. | |
| 2003/0236505 A1 | 12/2003 | Bonadio et al. | |
| 2003/0236549 A1 | 12/2003 | Bonadio et al. | |
| 2004/0193008 A1 | 9/2004 | Jaffe et al. | |
| 2004/0193009 A1 | 9/2004 | Jaffe et al. | |

FOREIGN PATENT DOCUMENTS

| | | |
|---|---|---|
| WO | WO 99/51283 A2 | 10/1999 |
| WO | WO 99/59664 A1 | 11/1999 |
| WO | WO 00/54653 A1 | 9/2000 |
| WO | WO 01/67964 A3 | 9/2001 |
| WO | WO 01/70096 A1 | 9/2001 |
| WO | WO 01/70097 A1 | 9/2001 |
| WO | WO 02/024058 A2 | 3/2002 |
| WO | WO 02/024058 A3 | 3/2002 |
| WO | WO 02/39909 A1 | 5/2002 |
| WO | WO 02/068988 A1 | 9/2002 |
| WO | WO 02/069841 A2 | 9/2002 |
| WO | WO 2004/049905 A2 | 6/2004 |
| WO | WO 2004/071284 A1 | 8/2004 |
| WO | WO 2004/080313 A1 | 9/2004 |
| WO | WO 2004/084702 A2 | 10/2004 |

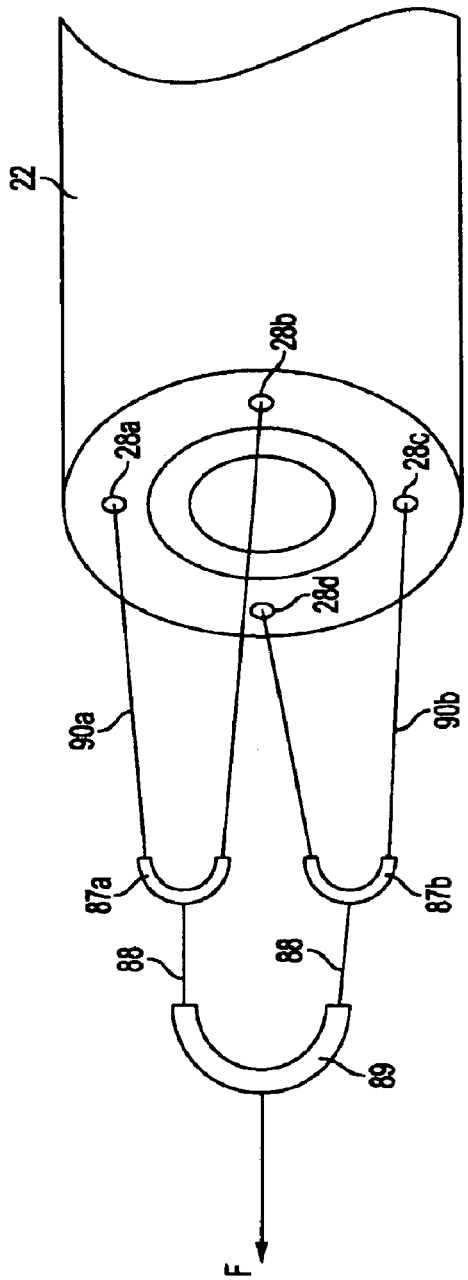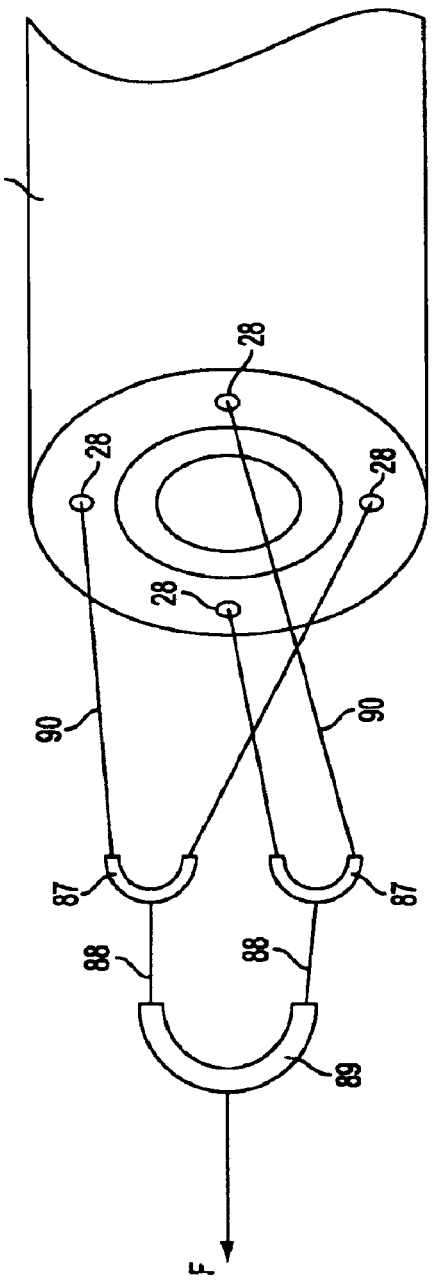
FIG. 10A
FIG. 10B

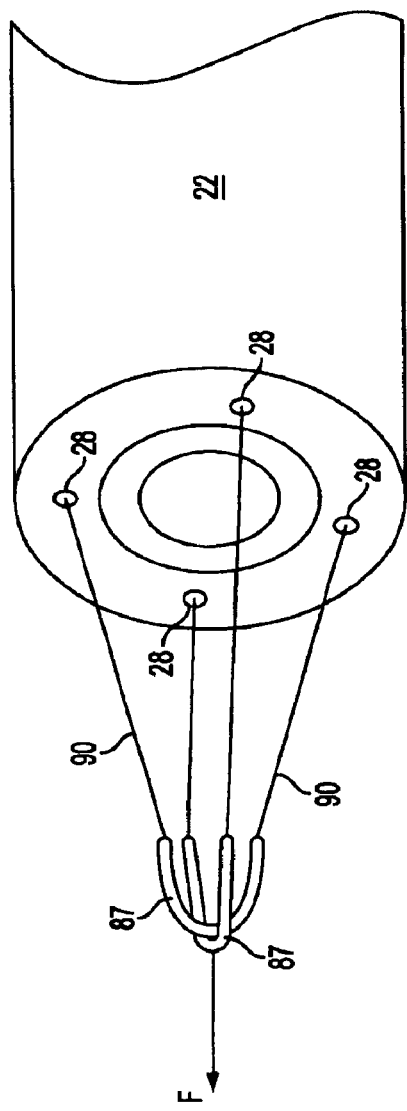
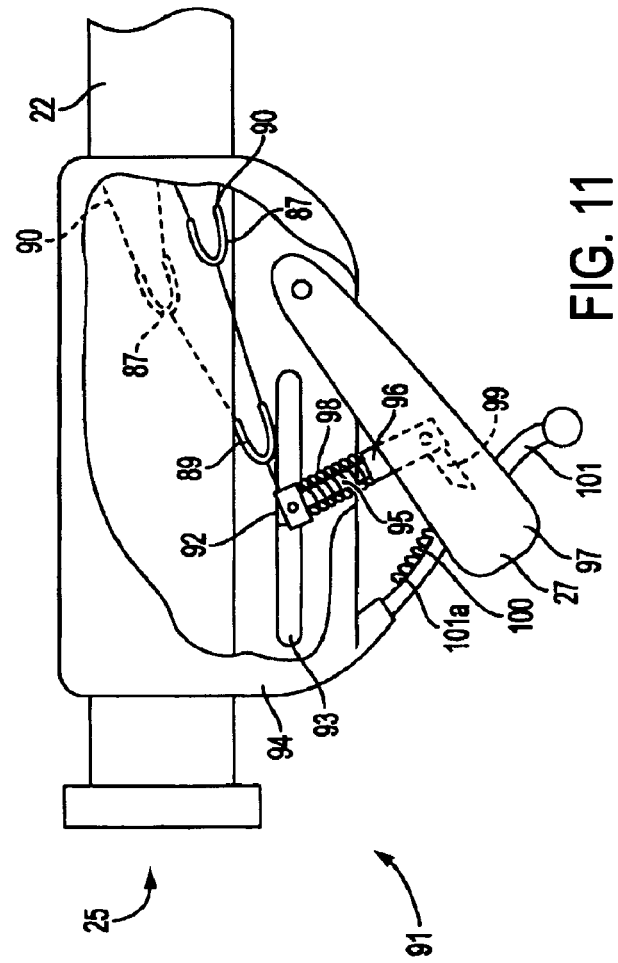

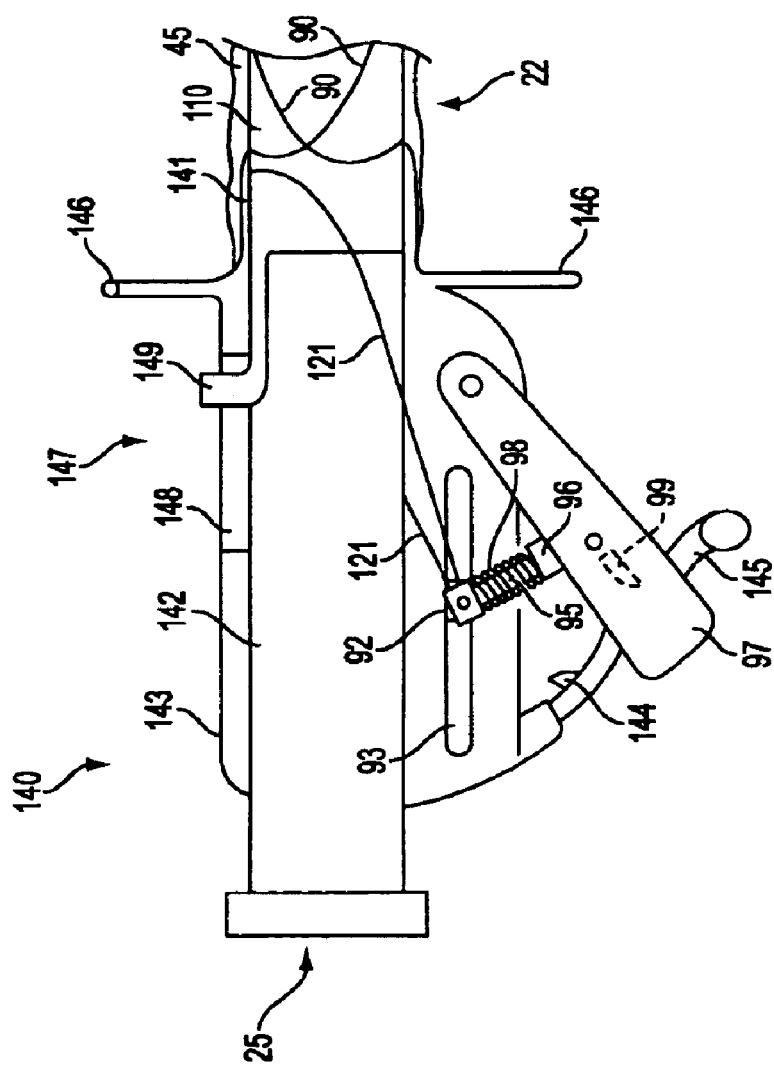

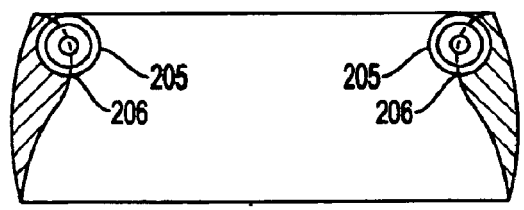 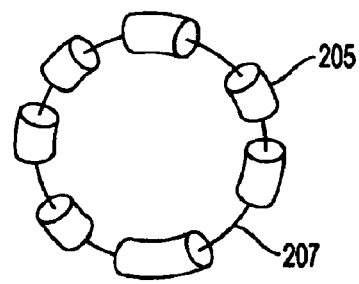
FIG. 17A  FIG. 17B
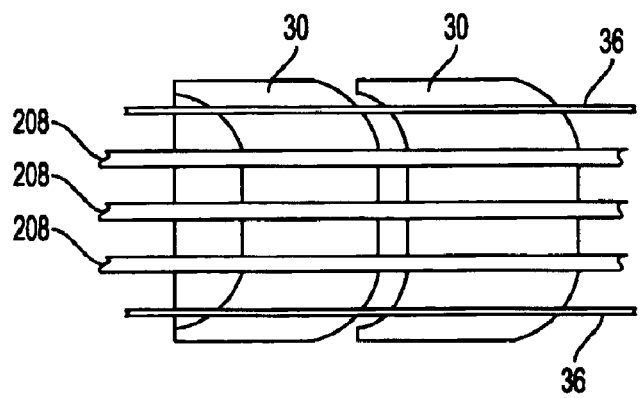 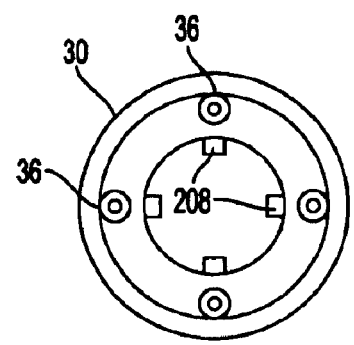
FIG. 18A  FIG. 18B

SHAPE LOCKABLE APPARATUS AND METHOD FOR ADVANCING AN INSTRUMENT THROUGH UNSUPPORTED ANATOMY

REFERENCE TO RELATED APPLICATIONS

This application is a continuation-in-part of U.S. patent application Ser. No. 10/173,203, Ser. No. 10/173,227, now U.S. Pat. No. 6,790,173 now U.S. Pat. No. 6,837,847 and Ser No. 10/173,220, now U.S. Pat. No. 6,783,491 all of which were filed Jun. 13, 2002 and are incorporated herein by reference in their entireties.

FIELD OF THE INVENTION

The present invention relates to apparatus and methods for placing and advancing a diagnostic or therapeutic instrument in a hollow body organ of unsupported anatomy, while reducing patient discomfort and risk of injury.

BACKGROUND OF THE INVENTION

The use of the colonoscope for examining the interior of the large intestine or colon is well-known. In general, a physician performing an examination or treatment of the colon inserts a colonoscope into the anus and then advances the colonoscope into the colon. A complete examination requires the physician to advance the colonoscope into the colon, negotiate the sigmoid colon, and left and right colic flexures up to the cecum. Advancement of the colonoscope is generally accomplished by manipulation of a steerable tip of the colonoscope, which is controlled at the proximal end of the device by the physician, in addition to torquing and pushing the scope forward or pulling it backward.

Problems regularly occur, however, when negotiating the colonoscope through the bends of the colon, such as at the sigmoid and left and right colic flexures. These problems arise because the colon is soft and has unpredictable fixation points to the viscera of the abdomen, and it is easily distensible. Consequently, after the steerable tip of the colonoscope is deflected to enter a new region of the colon, the principal direction of the force applied by the physician urging the proximal end of the device into the patient's colon is not in the direction of the steerable tip. Instead, the force is directed along the axis of the colonoscope towards the preceding bend(s), and causes yielding or displacement of the colon wall.

The loads imposed by the colonoscope on the colon wall can have a myriad of possible effects, ranging from patient discomfort to spastic cramp-like contractions of the colon and even possible perforation or dissection of the colon. Consequently, the colonoscope cannot be advanced as far as the cecum in up to one-sixth of all cases.

To address some of these difficulties, it is known to employ a guide tube that permits a colonoscope to be advanced through the rectum. One such device is described in U.S. Pat. No. 5,779,624 to Chang. An alternative approach calls for inserting the colonoscope through a curved region, and then mechanically actuating the portion of the device in the curved region to cause it to straighten, as described in U.S. Pat. No. 4,601,283 to Chikama.

Many patients find the operation of such previously-known devices unpleasant because the sigmoid portion of the colon is forced into an almost rectilinear shape by the guide tube. Due to the stiffness of the guide tube, careless handling of the guide tube presents a risk of injury to the colon.

Other previously-known apparatus and methods use an overtube having variable rigidity, so that the overtube may be inserted through curved anatomy in a flexible state, and then selectively stiffened to resist bending forces generated by passing a colonoscope through the overtube. One example of such a device is described in U.S. Pat. No. 5,337,733 to Bauerfiend. The device described in that patent comprises inner and outer walls having opposing ribs spaced apart across an air-filled annulus. The ribs are selectively drawn together to intermesh, and form a rigid structure by evacuating the annulus.

Another previously-known endoscopic device for delivering aneurysm clips within a hollow organ or vessel is described in U.S. Pat. No. 5,174,276 to Crockard. The device described in that patent includes a conduit formed from a multiplicity of elements that are capable of angulation relative to one another, and which becomes rigid when subjected to a tensile force. The device is described as being particularly useful in neurosurgery, where the variable rigidity of the device is useful for providing a stable platform for neurosurgical interventions, such as clipping an aneurysm.

While previously-known apparatus and methods provide some suggestions for solving the difficulties encountered in advancing diagnostic or therapeutic instruments through easily distensible body organs, few devices are commercially available. Although the precise reasons for this lack of success are uncertain, previously-known devices appear to pose several problems.

For example, the devices described in the Bauerfiend and Crockard patents appear to pose a risk of capturing or pinching tissue between the endoscope/colonoscope and the distal end of the overtube or conduit when the scope is translated. Also, neither device provides any degree of steerability, and must be advanced along the pre-positioned scope. In addition, the bulk of the proximal tensioning system described in Crockard is expected to interfere with manipulation of the endoscope. Other drawbacks of previously-known devices may be related to the complexity or cost of such devices or the lack of suitable materials. In any event, there exists an un-met need for devices to solve this long-felt problem in the field of endoscopy and colonoscopy.

In view of the foregoing, it would be desirable to provide apparatus and methods for facilitating placement of diagnostic or therapeutic instruments within easily distensible hollow body organs, such as the esophagus or colon.

It further would be desirable to provide apparatus and methods that permit a diagnostic or therapeutic device to be advanced into a hollow body organ, and which facilitates passage of the device through tortuous anatomy without requiring straightening of organ passageways already traversed.

It also would be desirable to provide apparatus and methods for facilitating placement of diagnostic or therapeutic instruments within easily distensible hollow body organs that include means for reducing the risk that tissue will become inadvertently pinched between the apparatus and the advancing or withdrawing instrument, or caught as the diagnostic or therapeutic instrument is maneuvered through the hollow body organ.

It still further would be desirable to provide apparatus and methods that provide a low-cost, single use, easily manufacturable guide for inserting a diagnostic or therapeutic instrument in a hollow body organ.

It yet further would be desirable to provide apparatus and methods that provide a low-cost, easily manufacturable guide for inserting a diagnostic or therapeutic instrument in a hollow body organ, wherein a portion of the apparatus is disposable after a single use and a remaining portion of the device is re-usable.

Still further, it would be desirable to provide a device having a selectively locking shape for inserting a diagnostic or therapeutic instrument in a hollow body organ, but which facilitates manipulation of a proximal end of the diagnostic or therapeutic instrument.

It additionally would be desirable to permit multiple diagnostic or therapeutic devices to be positioned in a hollow, unsupported organ, so that at least one of the devices may be withdrawn and repositioned while the other devices are retained in place.

It further would be desirable to provide apparatus and methods for facilitating placement of diagnostic or therapeutic instruments within easily distensible hollow body organs that reduces the risk of reconfiguration of the apparatus in the event of failure of the device.

It yet further would be desirable to provide apparatus and methods for facilitating placement of diagnostic or therapeutic instruments within easily distensible hollow body organs that substantially maintains an axial length of the apparatus.

SUMMARY OF THE INVENTION

In view of the foregoing, it is an object of the present invention to provide apparatus and methods for facilitating placement of diagnostic or therapeutic instruments within easily distensible or unpredictably supported hollow body organs, such as the esophagus or colon.

It is a further object of the present invention to provide apparatus and methods that permit a diagnostic or therapeutic device to be advanced into a hollow body organ, and which facilitates passage of the device through tortuous anatomy without requiring straightening of organ passageways already traversed.

It also is an object of the present invention to provide apparatus and methods for facilitating placement of diagnostic or therapeutic instruments within easily distensible hollow body organs that include means for reducing the risk that tissue will become inadvertently pinched or caught as the diagnostic or therapeutic instrument is maneuvered through the hollow body organ.

It is a still further object of the present invention to provide apparatus and methods that provide a low-cost, single use, easily manufacturable guide for inserting a diagnostic or therapeutic instrument in a hollow body organ.

It is another object of this invention to provide apparatus and methods that provide a low-cost, easily manufacturable guide for inserting a diagnostic or therapeutic instrument in a hollow body organ wherein a portion of the apparatus is disposable after a single use and a remaining portion of the device is re-usable.

Still further, it is an object of the present invention to provide a device having a selectively locking shape for inserting a diagnostic or therapeutic instrument in a hollow body organ, but which facilitates manipulation of a proximal end of the diagnostic or therapeutic instrument.

It is yet another object of the present invention to permit multiple diagnostic or therapeutic devices to be positioned in a hollow, unsupported organ, so that at least one of the devices may be withdrawn and repositioned while the other devices are retained in place.

It is a further object of the present invention to provide apparatus and methods for facilitating placement of diagnostic or therapeutic instruments within easily distensible hollow body organs that reduces the risk of reconfiguration of the apparatus in the event of failure of the device.

It is a still further object of the present invention to provide apparatus and methods for facilitating placement of diagnostic or therapeutic instruments within easily distensible hollow body organs that substantially maintains an axial length of the apparatus.

These and other objects of the present invention are attained by providing apparatus comprising a proximal handle, an overtube coupled to the proximal handle and having a distal region, an atraumatic tip disposed on the distal region, and mechanisms for selectively locking the shape of the overtube to assist one or more diagnostic or therapeutic instruments to negotiate the tortuous or unsupported anatomy of a hollow body organ, rather than distending the wall of the organ. The apparatus includes a main lumen extending between the handle, overtube and atraumatic tip, through which a diagnostic or therapeutic instrument, such as an endoscope or colonoscope, may be translated.

The handle extends from the patient, e.g., through the mouth or anus, where it can be manipulated by the physician. The proximal handle may form part of a single use, disposable apparatus, or may be separable from the overtube and reusable. Alternatively, the overtube may include a disposable single-use cover that fits over a reusable structure. The overtube may be angled relative to a working axis of the handle, so that the handle does not interfere with manipulation of the diagnostic or therapeutic instrument inserted through the overtube.

An overtube constructed in accordance with the principles of the present invention may comprise a multiplicity of nested elements that are selectively-tensionable by actuation of a ratchet, a pneumatic mechanism, or shape memory materials. Alternatively, the overtube may include a series of interconnected links surrounded by a selectively actuable clamping mechanism, a tubular member comprising a multiplicity of helical links formed from a material having variable durometer and surrounded by a clamping mechanism, a thermo-responsive polymer or alloy, an elongate, flexible tube made from an electroactive polymer, or a series of overlapping or nested links that are made from a shape memory material. The overtube may include any of a number of aids for facilitating passage of the diagnostic or therapeutic instrument through the main lumen, including a lubricious liner, rails or rollers.

The tensioning systems may provide a fail-safe mode that reduces the risk of reconfiguration of the overtube in the event that the mechanism fails. The fail-safe mode may equalize compressive clamping loads applied to the overtube when the overtube is rigidized, and be configured to rigidize the overtube without substantial proximal movement of the distal region.

The liner may be made from thin, flexible material, have a hydrophilic coating, incorporate a kink-resistant coil, or combinations thereof. Alternatively, the liner may be a disposable sheath that may be removed from the overtube to permit re-use of the internal structure of the overtube.

The atraumatic tip of the present invention preferably is configured to reduce the risk of capturing or pinching tissue between the overtube and a diagnostic or therapeutic instrument that is selectively translated through the overtube. This is preferably accomplished by the atraumatic tip applying a radially-outwardly directed load to the wall of the hollow body organ in the vicinity of the distal region where the diagnostic or therapeutic instrument exits the apparatus.

In addition, the distal region of the overtube preferably includes a flexible portion that permits a steerable tip of a diagnostic or therapeutic device disposed within the distal region to deflect the distal region of the overtube in a desired direction. This permits the overtube to be readily advanced together with the steerable tip of the diagnostic or therapeutic device.

BRIEF DESCRIPTION OF THE DRAWINGS

Further features of the invention, its nature and various advantages will be more apparent from the accompanying drawings and the following detailed description of the preferred embodiments, in which:

FIGS. 10A–10C are schematic views of components of a tensioning mechanism suitable for rigidizing the overtube of the present invention, wherein the components provide a fail-safe mode;

FIG. 11 is a cut-away side view of a tensioning mechanism incorporating the components of FIGS. 10A and 10B within the handle of the apparatus of FIG. 2;

FIGS. 13A and 13B are, respectively, a side sectional view of a tensioning mechanism incorporating the pulley manifold of FIG. 12B within the handle of the apparatus of FIG. 2, and an indicator that displays the status of the overtube;

FIGS. 17A and 17B, respectively, are a side-section view of an alternative element suitable for use in the overtube of FIG. 2 and a roller element suitable for use with the element of FIG. 17A, respectively;

FIGS. 18A and 18B depict the use of lubricious rails in the overtube of the apparatus of FIG. 2 or 9 to facilitate passage of a diagnostic or therapeutic device through the main lumen;

DETAILED DESCRIPTION OF THE INVENTION

Figure 1:
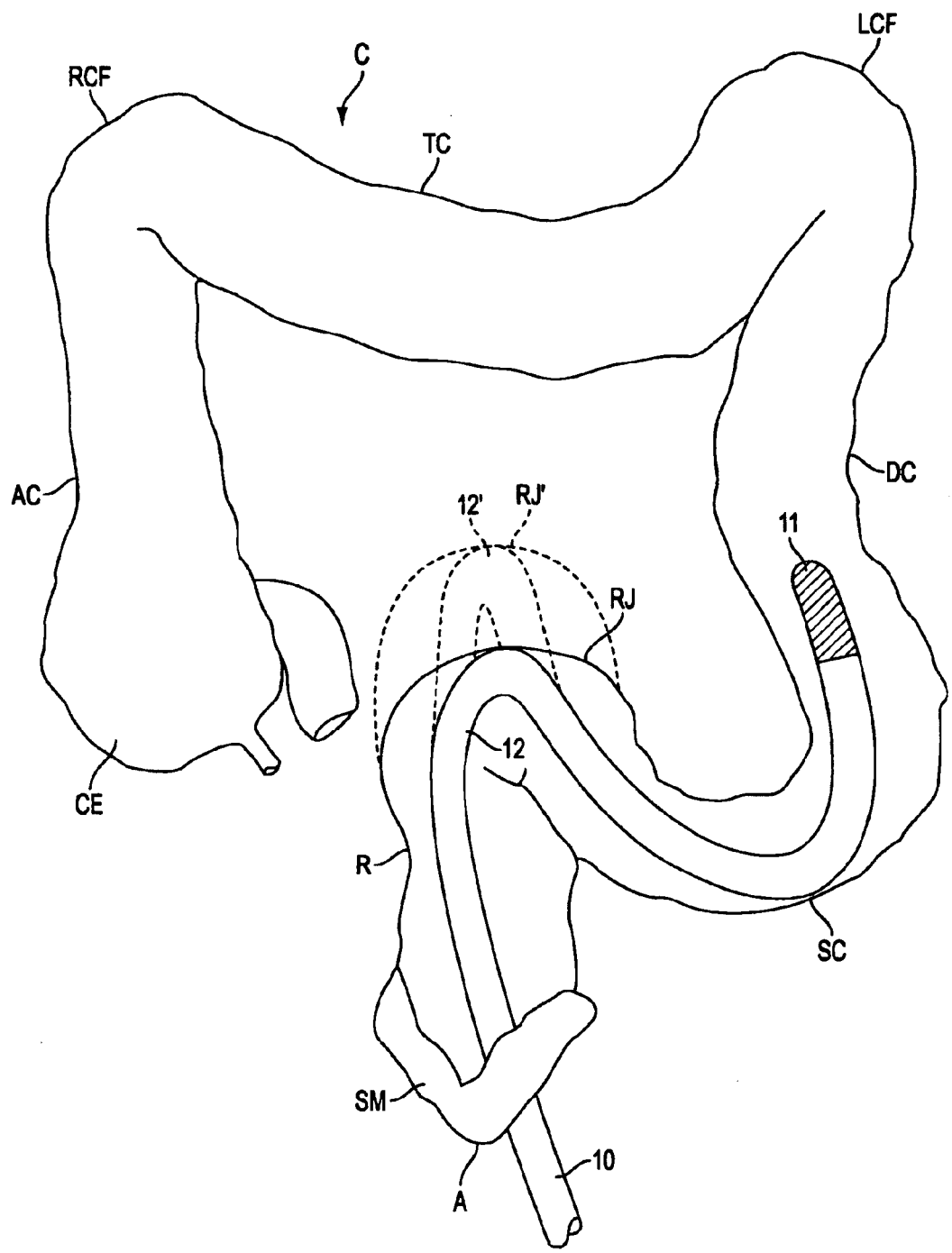
FIG. 1 is a schematic view of a human colon illustrating a common difficulty encountered in advancing a colonoscope beyond the sigmoid colon.

Referring to FIG. 1, problems associated with previously-known apparatus and methods for inserting and advancing a diagnostic or therapeutic instrument into a hollow body organ having tortuous or unsupported anatomy, illustratively, patient's colon C, are described. Colon C includes sphincter muscle SM disposed between anus A and rectum R. Rectum R is coupled via the rectosigmoid junction RJ to sigmoid colon SC. Sigmoid colon SC joins descending colon DC, which in turn is coupled to transverse colon TC via left colic flexure LCF. Transverse colon TC also is coupled by right colic flexure RCF to ascending colon AC and cecum CE, which receives waste products from the small intestine.

As illustrated in FIG. 1, colonoscope 10 having steerable distal tip 11 is typically inserted through anus A into rectum R, and then steered through rectosigmoid junction RJ into sigmoid colon SC. As depicted in FIG. 1, distal tip 11 of colonoscope 10 is advanced through sigmoid colon SC and deflected into descending colon DC. Further urging of the colonoscope by the physician can cause region 12 of the colonoscope to bear against and cause displacement of the rectosigmoid junction RJ, as illustrated by dotted lines 12' and RJ' in FIG. 1.

Such distension may result in patient discomfort or spasm, and if unnoticed, could result in injury to the colon. The potential for movement of colonoscope to cause distension, discomfort or spasm is also great where the colonoscope must negotiate left colic flexure LCF and right colic flexure RCF, and results in a large portion of such examinations terminating before the physician can advance distal tip 11 to cecum CE.

The present invention provides apparatus and methods for placing a diagnostic or therapeutic instrument through the tortuous or unpredictably supported anatomy of a hollow body organ, such as the esophagus or colon, while reducing the risk of distending or injuring the organ. Apparatus constructed in accordance with the present invention permits an endoscope or colonoscope to be readily advanced into a patient's tortuous or unsupported anatomy by selectively shape-fixing an overtube portion of the apparatus, while also preventing tissue from being captured or pinched between the overtube and scope.

Figure 2:
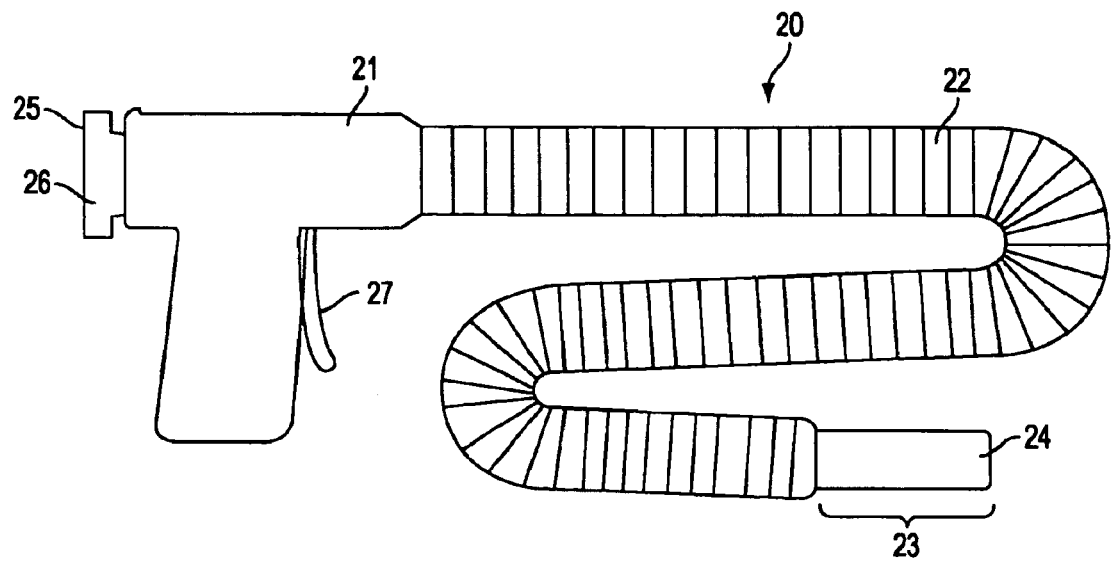
FIG. 2 is a side view of illustrative apparatus of the present invention.

Referring now to FIG. 2, apparatus 20 of the present invention is described. Apparatus 20 comprises handle 21, overtube 22, and distal region 23 having atraumatic tip 24. Handle 21 includes lumen 25 that extends from Toughy-Borst valve 26 through overtube 22, distal region 23 and atraumatic tip 24. Lumen 25 is configured to facilitate passage of a standard commercially available colonoscope, such as colonoscope 10, therethrough. Toughy-Borst valve 26 may be actuated to releasably lock colonoscope 10 to apparatus 20 when colonoscope 10 is inserted within lumen 25. As described hereinafter, overtube 22 is configured so that it can be selectively transitioned between a flexible state and a rigid, shape-fixed state by actuator 27 disposed on handle 21.

Figure 3A:
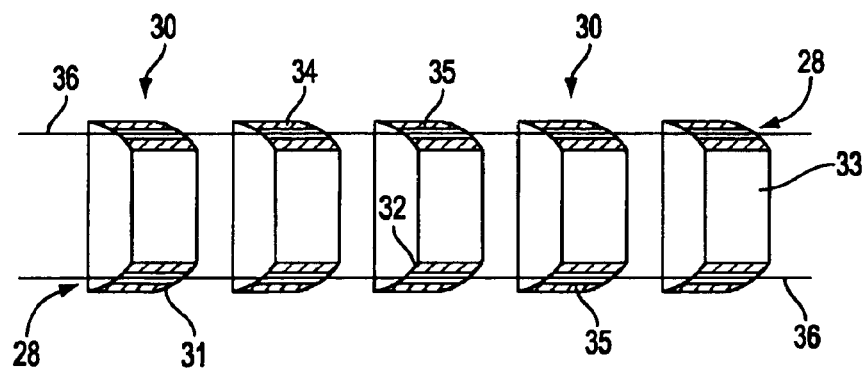
FIG. 3A is a side-sectional exploded view of nestable elements of a first embodiment of an overtube suitable for use in the apparatus of FIG. 2.

In FIG. 3A, illustrative embodiment of overtube 22 comprises a multiplicity of nestable elements 30. For purposes of illustration, nestable elements 30 are shown spaced-apart, but it should be understood that elements 30 are disposed so that distal surface 31 of one element 30 coacts with proximal surface 32 of an adjacent element. Each of nestable elements 30 has central bore 33 to accommodate colonoscope 10, and preferably two or more tension wire bores 35. When assembled as shown in FIG. 2, nestable elements 30 are fastened with distal and proximal surfaces 31 and 32 disposed in a coacting fashion by a plurality of tension wires 36 that extend through tension wire lumens 28 defined by tension wire bores 35. Tension wires 36 preferably are made from a superelastic material, e.g., nickel titanium alloy, to provide flexibility, kink-resistance and smooth movement of the tension wires through tension wire bores 35. Alternatively, the tension wires may be made from braided stainless steel, a single stainless steel wire, Kevlar, a high tensile strength monofilament thread, or combinations thereof. These materials are provided only for the sake of illustration and should in no way be construed as limiting.

In a preferred embodiment, a ratio of the diameter of tension wires 36 to the diameter of tension wire bores 35 approximately is in a range of ½ to ⅔. Applicants have observed that this provides smooth relative movement between the tension wires and the nestable elements, even when overtube 22 is retroflexed. While a greater ratio is desirable, such a configuration appears to cause the edges of tension wire bores 35 to gouge into tension wires 36, thereby constraining movement of the tension wires through the tension wire bores. Conversely, while applicants contemplate that a smaller ratio would provide even smoother relative movement, the resultant increase in the thickness of wall 34 of each nestable element 30 is undesirable.

In a preferred embodiment, adjacent surfaces 31 and 32 of each nestable element 30 are contoured to mate with the next adjacent element, so that when tension wires 33 are relaxed, surfaces 31 and 32 can rotate relative to one another. Tension wires 36 are fixedly connected to the distal end of overtube 22 at the distal ends and to a tensioning mechanism disposed within handle 21 at the proximal ends. When actuated by actuator 27, tension wires 36 impose a load that clamps distal and proximal surfaces 31 and 32 of nestable elements 30 together at the current relative orientation, thereby fixing the shape of overtube 22.

When the load in tension wires 36 is released, tension wires 36 provides for relative angular movement between nestable elements 30. This in turn renders overtube 22 sufficiently flexible to negotiate a tortuous path through the colon. When the tensioning mechanism is actuated, however, tension wires 36 are retracted proximally to apply a clamping load to the nestable elements. This load prevents further relative movement between adjacent elements 30, and stiffens overtube 22 so that any distally directed force applied to colonoscope 10 causes distal tip 11 to advance further into the colon, rather than cause overtube 22 to bear against the wall of the colon. The shape-fixed overtube absorbs and distributes vector forces, shielding the colon wall.

In a preferred embodiment, the radius of curvature of proximal surface 32 closely approximates the radius of curvature of distal surface 31. In particular, a ratio of the radius of curvature of distal surface 31 to that of proximal surface 32 is in an approximate range of about 0.9 to 1.0. Furthermore, the coefficient of static friction between the distal and proximal surfaces preferably is in an approximate range of 0.2 to 1.4 (based on ASTM standard D1894). This structure appears to permit sufficient frictional force to develop between the surfaces to prevent relative movement between adjacent elements when overtube 22 is rigidized.

Figure 3B:
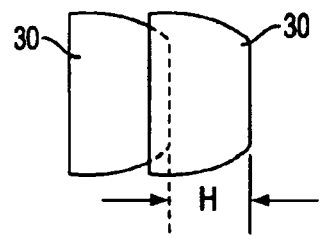
FIG. 3B is a side view of two of the nestable elements of FIG. 3A nested together.

Nestable elements 30 may be configured to provide a stack-up of overtube 22 that is a function of the growth height. As defined in FIG. 3B, growth height H is the increase in the longitudinal length of overtube 22 when one nestable element 30 is nested within another nestable element 30. To accommodate the radius of curvature obtainable by standard commercially available colonoscopes, growth height H preferably is less than or equal to about 0.31 in, and more preferably about 0.16 in. This provides overtube 22 with sufficient flexibility to assume a radius of curvature that is less than or equal to approximately 0.95 in. If overtube 22 needs to accommodate other endoscopes or medical instruments that are larger or smaller in size and/or that may assume different radii of curvature, or the overtube needs to accommodate tighter anatomical constraints, applicants contemplate that growth height H may be increased or decreased proportionate to the change in dimensions of overtube 22. Applicants note that the preceding geometrical characterization of nestable element 30 does not account for material interference or effects to the tension wire bores, which are omitted from FIG. 3B for illustrative purposes.

Nestable elements 30 preferably are molded from a polymer filled with fibers of glass, carbon, or combinations thereof. In a particularly useful embodiment, nestable elements 30 are molded from polyurethane filled with 20–40% by volume of glass fibers, 20–40% by volume of carbon fibers, or 20–40% by volume of glass and carbon fibers. One example is isoplast 2540, which is available from Dow Chemicals, Midland, Mich. Applicants have observed that such materials enhance friction between adjacent elements, which advantageously reduces the risk of relative angular movement between the adjacent elements when overtube 22 is stiffened and, thus, reduces the risk of undesired reconfiguration of overtube 22 in its shape-locked state. While a greater amount of glass and/or carbon fibers is desirable, such a material appears to reduce the structural integrity of the nestable element.

Furthermore, fiber embedded polymers increase the rigidity of nestable elements 30 so that longitudinal contraction of overtube 22 is significantly reduced when the overtube is stiffened. Longitudinal contraction develops when tension wires 36 are actuated to apply a compressive clamping load to overtube 22. The resultant pressure eliminates any gaps between adjacent elements 30 and deflects the proximal portion of each nestable element radially outward. This foreshortens each element in the longitudinal direction, so that overtube 22 contracts in the axial length.

Typically, an overtube made from polymeric nestable elements without inclusion of glass and/or carbon fibers will contract approximately 8–12% in the longitudinal direction when a compressive force of approximately 30 lbs is applied. By comparison, when a compressive load of 30 lbs is applied to nestable elements made from a glass and/or carbon fiber embedded polymer, as in the preferred embodiment of the present invention, the overtube only contracts approximately 4%. Advantageously, this reduces trauma to the patient by providing greater accuracy during use of the present invention, which is particularly important in delicate procedures. In addition to glass and/or carbon filled polymers, it will be apparent to one of ordinary skill in the art that nestable elements 30 also may be molded or machined from other polymers and/or metals, such as polyurethane, polyvinyl chloride, polycarbonate, nylon, titanium, tungsten, stainless steel, aluminum, or combinations thereof. Indeed, nestable elements 30 made from metals experience a longitudinal contraction even less than that experienced by fiber embedded polymers. These materials are provided only for the sake of illustration, and one of ordinary skill in the art will recognize numerous additional materials that are suitable for use with the apparatus of the present invention.

Figure 4:
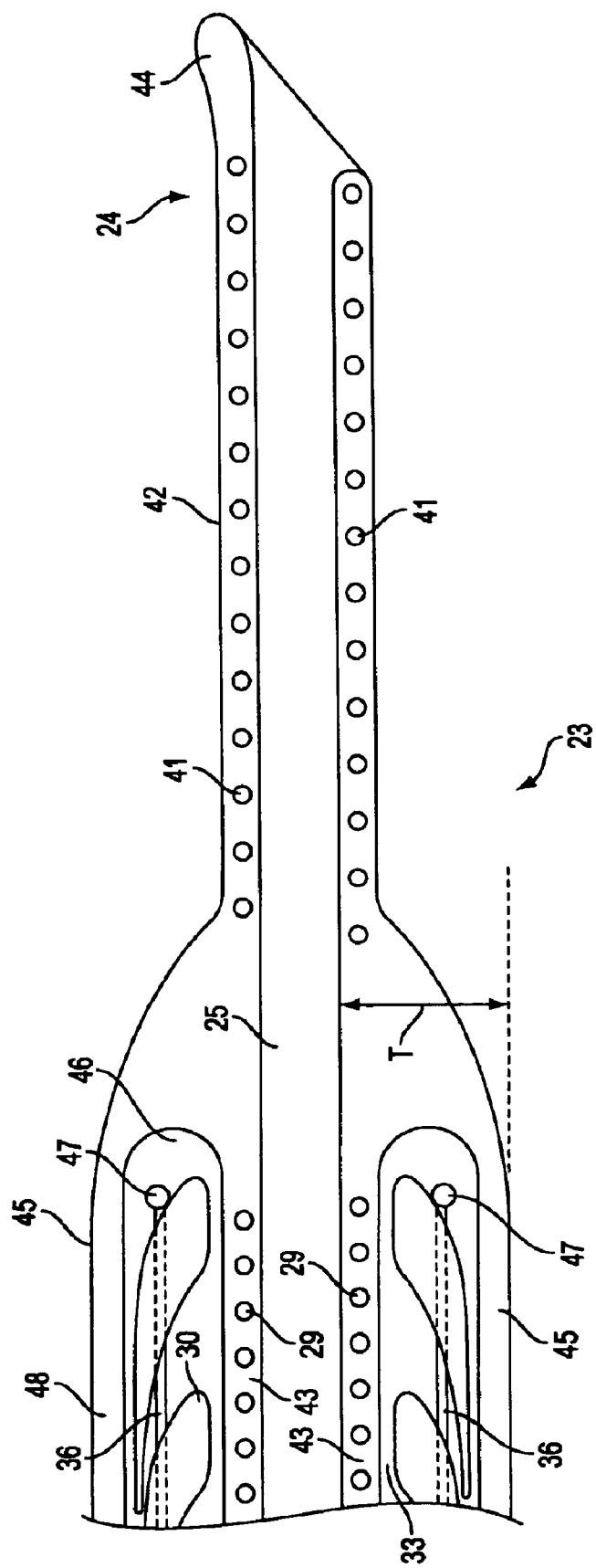
FIG. 4 is a side-sectional view of a distal region of the apparatus of FIG. 2 constructed in accordance with principles of the present invention.

Referring now to FIG. 4, an illustrative embodiment of distal region 23 and atraumatic tip 24 is described. Distal region 23 comprises flexible, kink-resistant coil 41 encapsulated in flexible layer 42. Layer 42 preferably comprises a soft elastomeric and hydrophilic coated material, such as silicon or synthetic rubber, and terminates at the distal end in enlarged section 44 that forms atraumatic tip 24. At the proximal end, layer 42 joins with or is integrally formed with liner 43 that extends through bores 33 of nestable elements 30 to handle 21. In a preferred embodiment, liner 43 is made of a thin, flexible material optionally having flexible, kink-resistant coil 29 embedded therein. The material of liner 43 preferably has a high durometer within the range of 30–80D, but also may have a lower or higher durometer.

Layer 42 preferably joins with or is integrally formed with flexible elastomeric skin 45 to form sheath 48, which encapsulates nestable elements 30 in annular chamber 46. Skin 45 provides a relatively smooth outer surface for overtube 22, and prevents tissue from being captured or pinched during relative rotation of adjacent nestable elements 30. In a preferred embodiment, aggregate thickness T of skin 45, nestable elements 30 and liner 43, is less than or equal to approximately 2.5 mm, and more preferably less than or equal to 1 mm. For example, skin 45 may have a thickness of 0.13 mm, or more preferably 0.1 mm, element 30 may have a thickness of 1.9 mm, and more preferably 0.7 mm, and liner 43 may have a thickness of 0.38 in, or more preferably 0.15 mm.

In accordance with one aspect of the present invention, colonoscope 10 may be positioned with its distal tip 11 disposed in distal region 23, so that deflection of steerable distal tip 11 imparts an angular deflection to distal region 23 and atraumatic tip 24. To ensure that there is no gross relative motion between colonoscope 10 and apparatus 20, Toughy-Borst valve 26 is tightened to engage apparatus 20 to the colonoscope. In this manner, colonoscope 10 and distal region 23 may be simultaneously advanced through the colon, with the distal tip of the colonoscope providing a steering capability to apparatus 20. Apparatus 20 therefore may be advantageously advanced together with colonoscope 10 when overtube 22 is in the flexible state, reducing relative motion between apparatus 20 and colonoscope 10 to those instances where overtube 22 must be shape-locked to prevent distension of the colon.

Still referring to FIG. 4, terminations 47 of tension wires are described. Terminations 47 illustratively comprise balls welded or molded onto the ends of tension wires 36 that ensure the tension wires cannot be pulled through tension wire bores 35 of the distal-most nestable element 30. This ensures that the nestable elements cannot come loose when overtube 22 is disposed within a patient.

Alternatively, terminations 47 may comprise knots formed in the ends of tension wires 36, or any suitable fastener that prevents the tension wires from being drawn through the tension wire bores of the distal-most nestable element. Advantageously, skin 45 provides additional assurance that all of nestable elements 30 can be safely retrieved from a patient's colon in the unlikely event of a tension wire failure.

Figure 5:
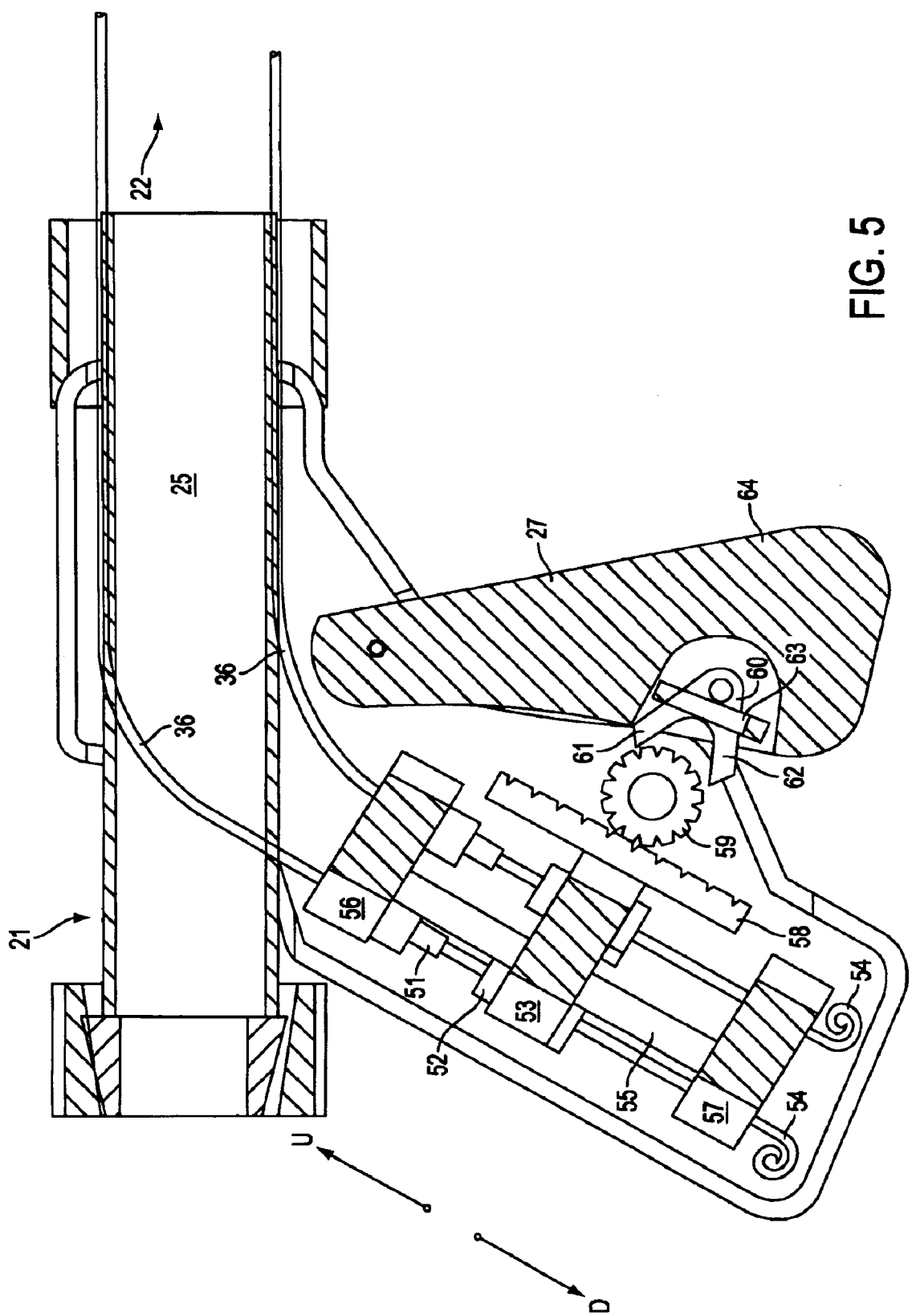
FIG. 5 is a side-sectional view of an illustrative arrangement of a mechanism suitable for use in the handle of the apparatus of FIG. 2.

Referring now to FIGS. 2 and 5, tension wires 36 within overtube 22, liner 43 and lumen 25 extend from distal region 23, through overtube 22, and to handle 21. Within handle 21, each tension wire 36 passes through wire lock release 51 fixedly attached to handle 21, and wire lock 52 disposed on slide block 53. Each tension wire 36 terminates at wire tension spring 54, which maintains tension wires 36 in light tension even when overtube 22 is in the flexible state. The degree of tension provided by wire tension springs 54 is not sufficient to clamp adjacent nestable elements 30 together, but on the other hand does not let gaps form between adjacent nestable elements, and helps to manage the tension wire take up or slack as overtube 22 makes various bends.

Slide block 53 is keyed to slide along rail 55 disposed between limit blocks 56 and 57, and comprises a rigid block having a bore through which rail 55 extends and an additional number of bores as required for the number of tension wires 36 employed. Rack gear 58 is fixedly coupled to slide block 53. Rack 58 mates with pinion gear 59, which is in turn driven by bi-directional pawl 60 coupled to actuator 27. Pinion gear 59 may be selectively engaged by either prong 61 or 62 of bi-directional pawl 60, depending upon the position of selector switch 63.

If prong 61 is selected to be engaged with pinion gear 59, a squeezing action applied to actuator 27, illustratively hand grip 64, causes rack 53 to move in the D direction in FIG. 5, thereby applying tension to tension wires 36. Repeated actuation of hand grip 64 causes slide block 53 to move progressively further in direction D, thereby applying an increasing clamping load on nestable elements 30. Any slack lengths of tension wires 36 extending below slide block 53 are taken up by wire tension springs 54. As discussed in greater detail below with respect to FIG. 6, wire locks 52, which are affixed to slide block 53, engage and retract tension wires 36 concurrently with movement of slide block 53 in the D direction.

If prong 62 is instead chosen by selector switch 63 to engage pinion gear 59, repeated actuation of hand grip 64 causes slide block 53 to translate in direction U, thereby relaxing the tensile load applied by tension wires 36 to nestable elements 30. Repeated actuation of hand grip 64 causes slide block 53 to advance in direction U until wire lock releases 51 engage wire locks 52, releasing all tension from tension wires 36 except that provided by wire tension springs 54. This action permits the clamping forces imposed on nestable elements 30 to be progressively reduced and render overtube 22 progressively move flexible, until when wire lock releases 51 engage wire locks 52, the overtube is returned to its most flexible state.

Figure 6:
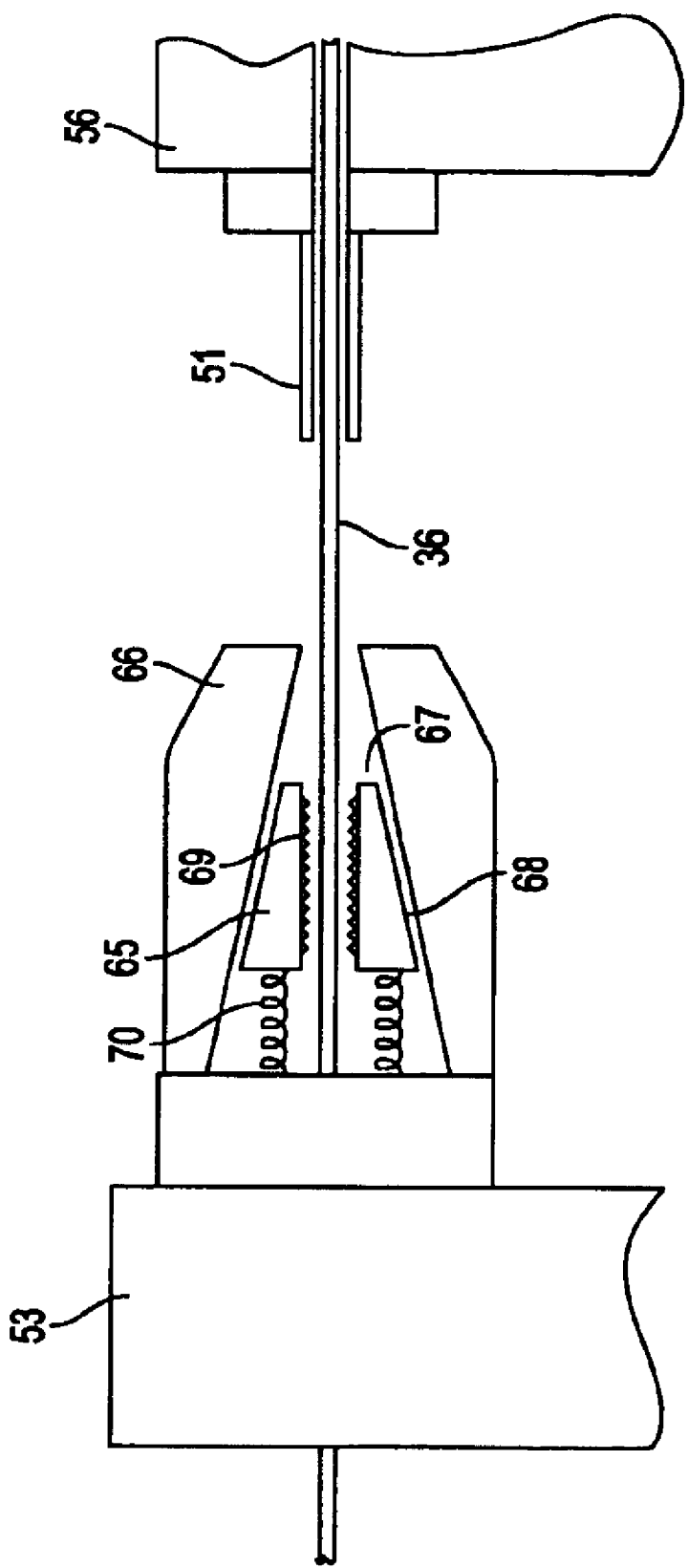
FIG. 6 is a side-sectional view of the detail of a wire clamping system suitable for use in the handle of FIG. 5.

Referring to FIG. 6, wire lock 52 and lock release 51 are described in greater detail. Wire lock 52 includes jaws 65 disposed within collet 66. Collet 66 includes a tapered conical bore 67. Jaws 65 have ramped exterior surfaces 68 and teeth 69, and are biased against the surface formed by the tapered conical bore by springs 70. Teeth 69 are configured to engage tension wire 36 under the bias force of springs 70. When slide block 53 is moved in direction D (see FIG. 5), jaws 65 engage and grasp tension wire 36 and retract the tension wire in direction D.

To disengage teeth 69 from tension wire 36, e.g., when it is desired to allow overtube 22 to return to a flexible state, slide block 53 is actuated as described previously to move in direction U. Further actuation of slide block 53 towards limit block 56 and wire lock release 51 causes wire lock release 51 to extend into tapered conical bore 67 and push jaws 65 backward against the bias of springs 70. Once tension wires 36 are freed from jaws 65, overtube 22 returns to its most flexible state.

Figure 7A:
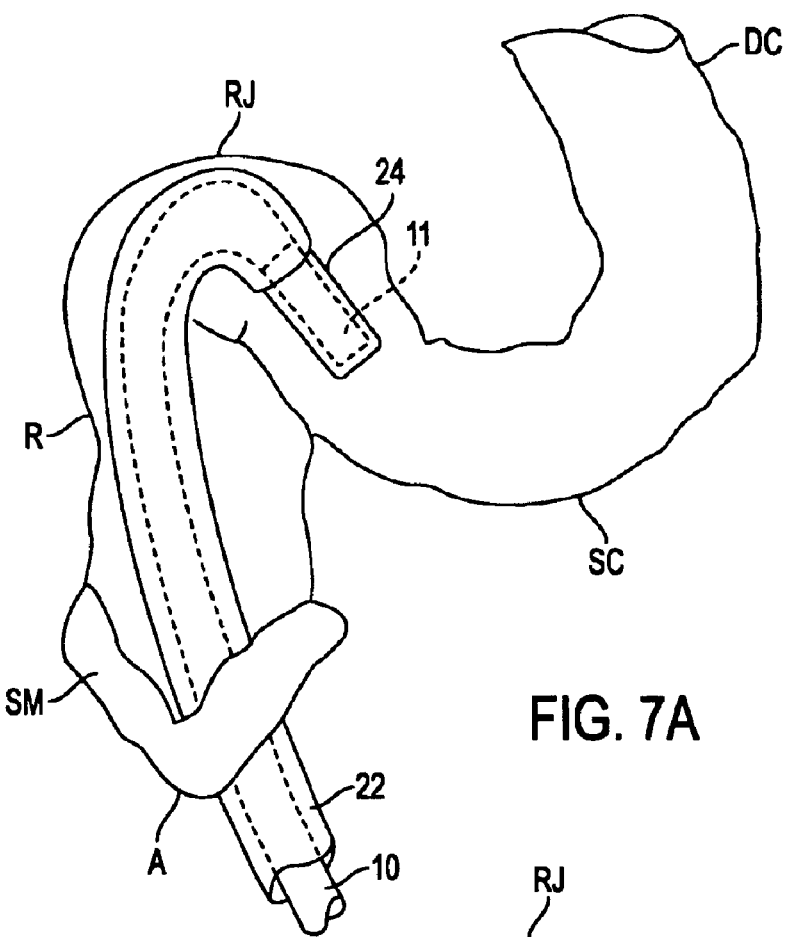
FIGS. 7A–7C are schematic views of a method of using the apparatus of the present invention.
Figure 7B:
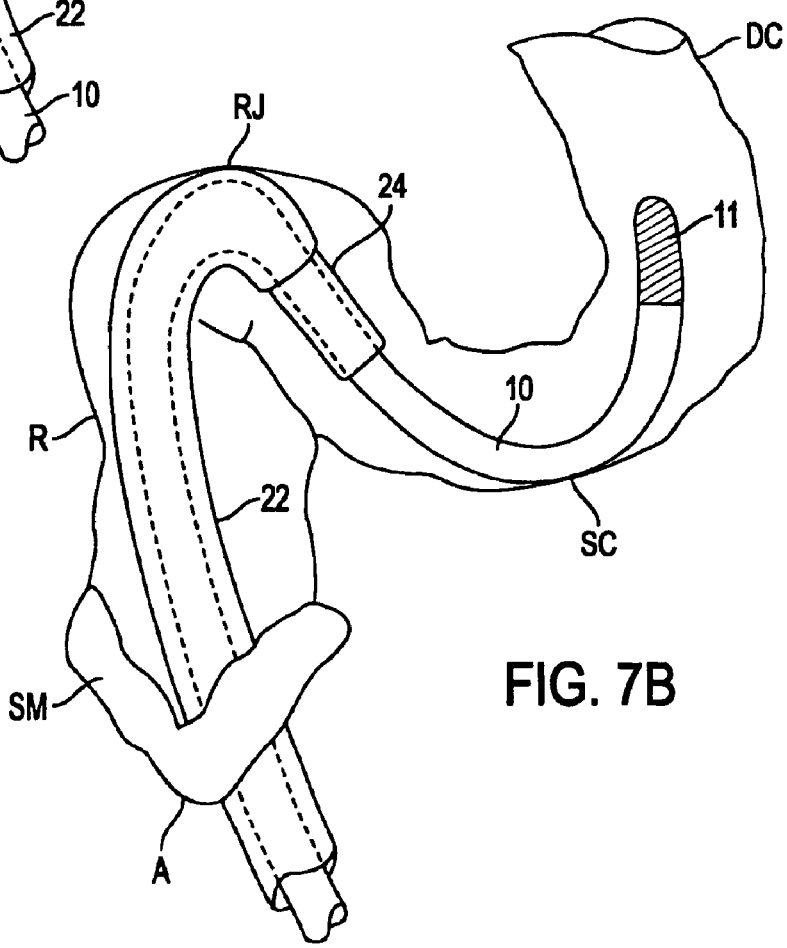
Figure 7C:
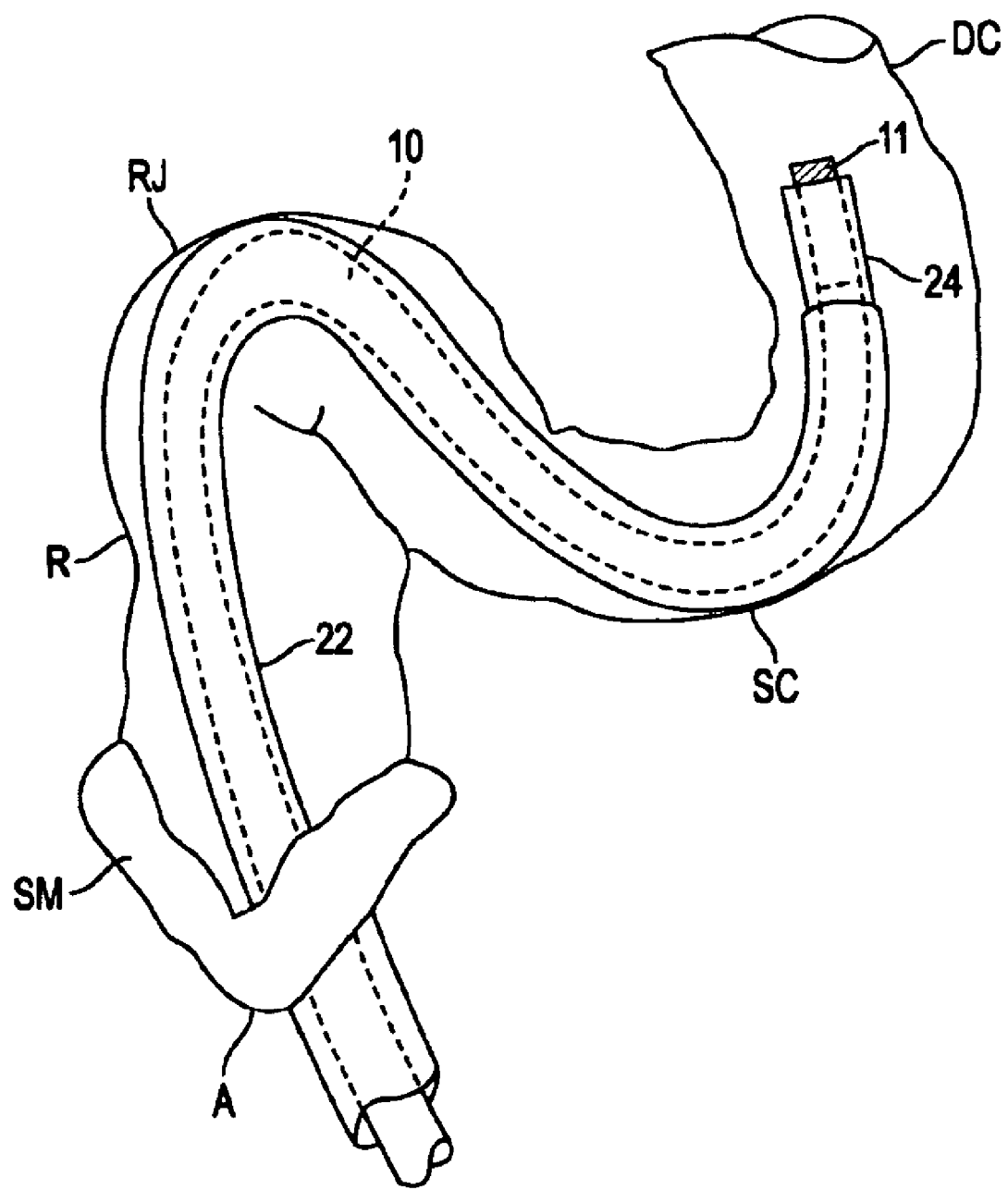

Referring to FIGS. 7A–7C, a method of using apparatus 20 is described. Colonoscope 10 and overtube 22 may be inserted into the patient either simultaneously or by first backloading the overtube onto the colonoscope. To perform simultaneous insertion, colonoscope 10 is introduced into lumen 25 of handle 21 until distal tip 11 of the colonoscope is disposed in distal region 23. Toughy-Borst valve 26 is actuated to lock apparatus 20 to colonoscope 10. As one unit, colonoscope 10 and overtube 22 are inserted into rectum R of the patient, and navigated about rectosigmoid junction RJ. As discussed previously, steerable distal tip 11 may be used to impart angular deflection to flexible tip 24 to steer tip 24 about tortuous curves, such as rectosigmoid junction RJ. Once distal tip 11 and tip 24 have been negotiated past rectosigmoid junction RJ, the current shape of overtube 22 is locked in the manner discussed above to provide a rigid channel through which colonoscope 10 may be further advanced into the colon without distending rectosigmoid junction RJ. Once distal tip 11 of colonoscope 10 is negotiated past sigmoid colon SC, overtube 22 is released from its rigid state and advanced along colonoscope 10 until it too traverses sigmoid colon SC. Again, the current shape of overtube 22 is locked to provide a rigid channel for advancement of colonoscope 10. To negotiate the remainder of the colon, such as left colic flexure LCF and right colic flexure RCF, the preceding steps may be repeated. In this manner, colonoscope 10 and overtube 22 may be navigated through the tortuous curves of the colon without distending the colon, and thereby causing discomfort, spasm or injury.

Figure 8:
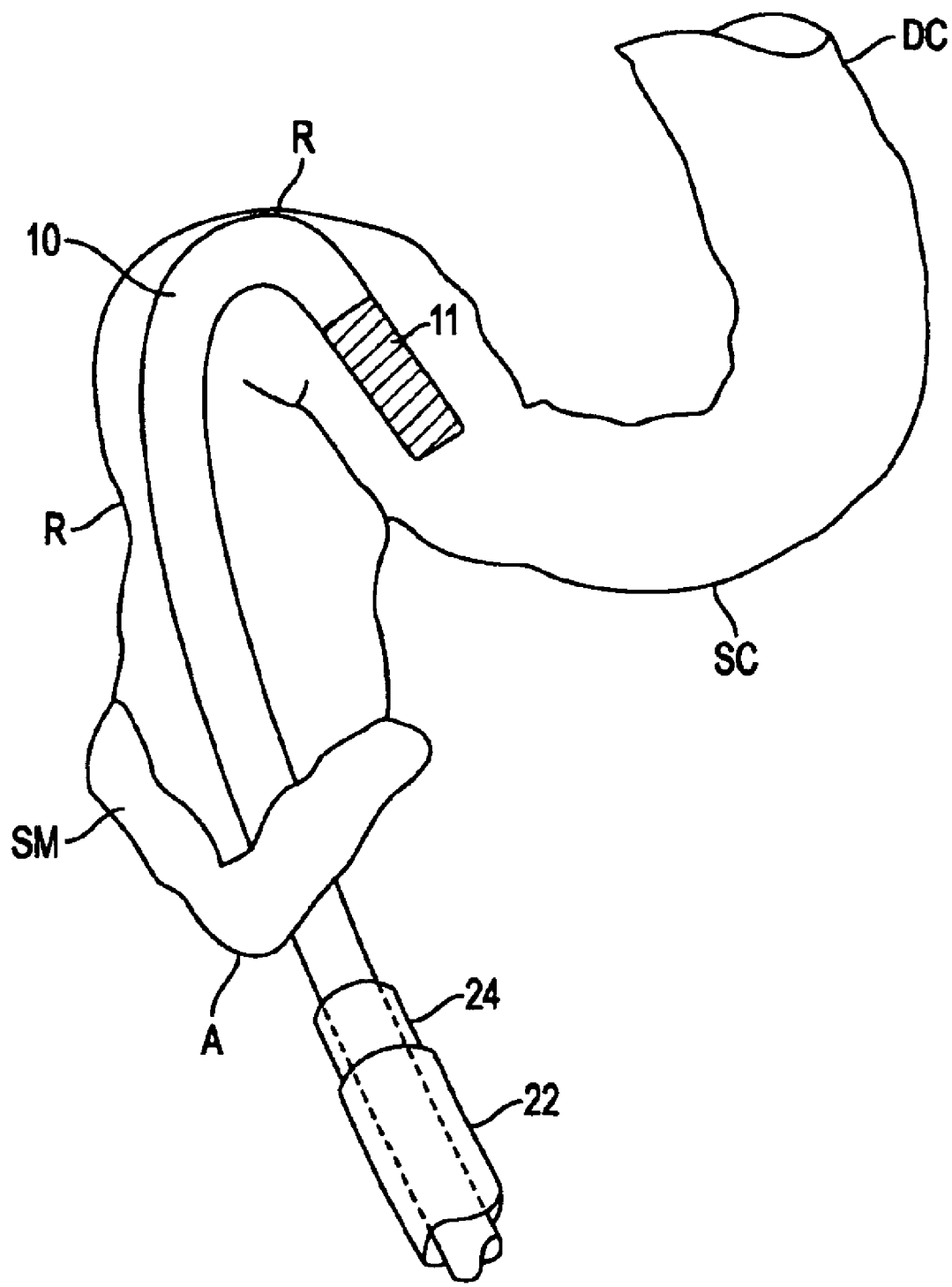
FIG. 8 is a schematic view of an alternative step in the method of using the apparatus of the present invention.

Alternatively, rather than simultaneously inserting both colonoscope 10 and overtube 22 into the patient, apparatus 20 first may be backloaded onto the colonoscope. First, overtube 22 is threaded onto colonoscope 10 and positioned proximal distal tip 11, as shown in FIG. 8. Colonoscope 10 then is inserted into rectum R of the patient and advanced around rectosigmoid junction RJ. Overtube 22 is advanced along colonoscope 10 into rectum R of the patient, using colonoscope 10 as a guide rail to negotiate rectosigmoid junction RJ. Once overtube 22 traverses rectosigmoid junction RJ to the position shown in FIG. 7A, the shape of overtube 22 is locked to provide a rigid channel through which colonoscope 10 may be further advanced into the colon. To negotiate the remainder of the colon, the steps discussed in reference to FIGS. 7B–7C may be performed.

Figure 9:
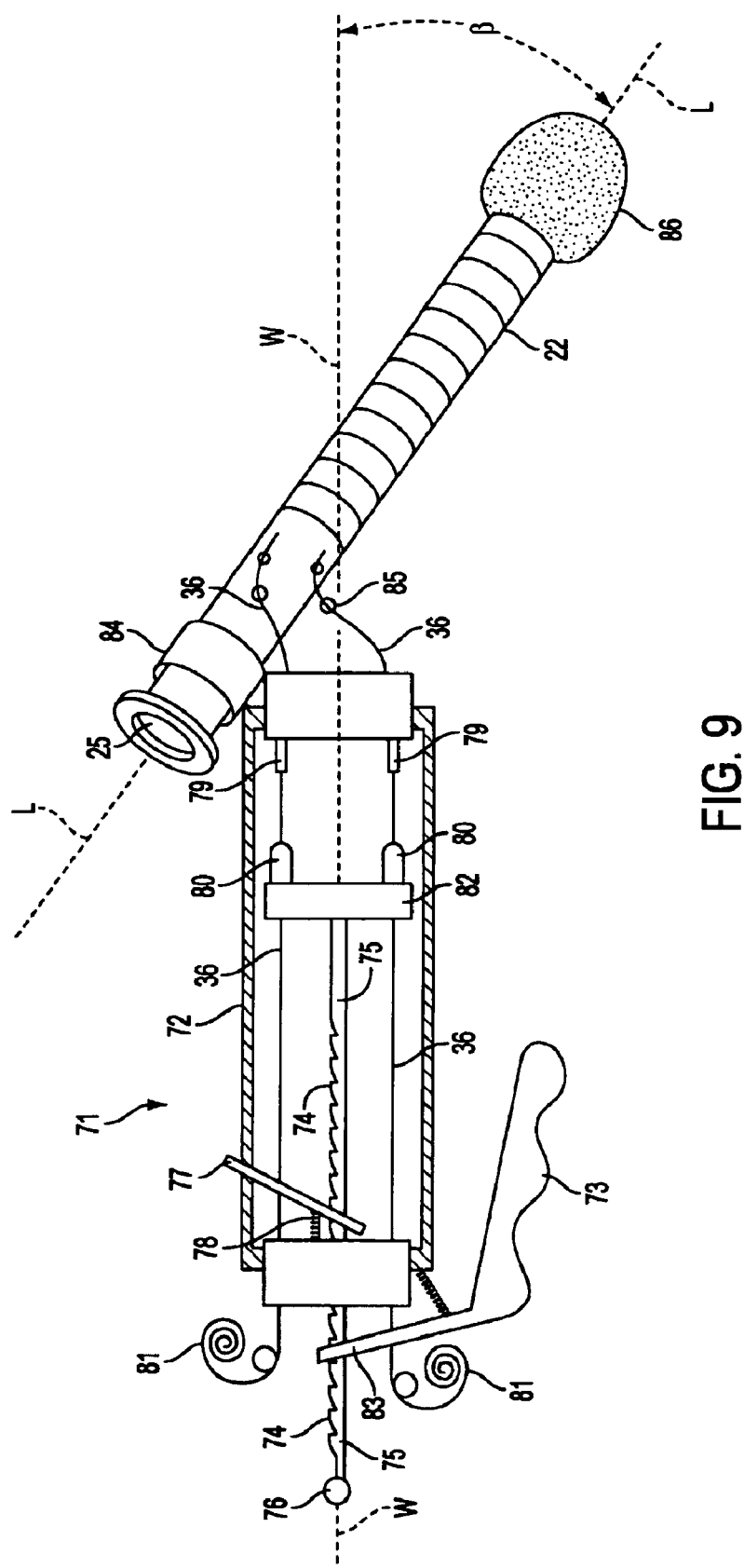
FIG. 9 is a side view of an alternative embodiment of the apparatus of the present invention.

With respect to FIG. 9, an alternative embodiment of handle 21 is described. Like handle 21 of FIG. 5, handle 71 also embodies a ratchet-type tension mechanism, but in this embodiment overtube 22 may be separated from handle 71, thereby permitting handle 71 to be sterilized for repeated use. Handle 71 comprises housing 72 having actuator 73 that engages teeth 74 disposed along the length of rod 75, which defines working axis W of handle 71. Push knob 76 is affixed to the proximal end of rod 75 so that when pawl 77 is released, rod 75 may be pushed in a distal direction. Pawl 77 engages teeth 74 of rod 75 to prevent distally-directed motion of rod 75. Spring 78 biases pawl 77 against teeth 74 of rod 75, to provide a one-way ratchet effect when actuator 73 is squeezed.

As in the embodiment of FIG. 5, tension wires 36 extend through wire lock releases 79, wire locks 80, and are coupled to wire tension springs 81. Wire locks 80 are affixed to block 82, which translates within housing 72 responsive to movement of rod 75. Wire locks 80 and wire lock releases 79 operate in the same manner as described with reference to FIG. 6.

In operation, squeezing actuator 73, illustratively a hand grip, causes fork 83 to move rod 75 in a proximal direction so that pawl 77 captures the next distal-most tooth 74. This movement also causes wire locks 80 to engage and grasp tension wires 36 and retract the tension wires proximally. Further actuation of actuator 73 causes overtube 22 to stiffen in the manner previously described. Spring 78 retains pawl 77 in continuous engagement with teeth 74, thereby preventing rod 75 from moving in the distal direction.

When it is desired to make overtube 22 more flexible, pawl 77 is released and knob 76 pushed in the distal direction so that wire locks 80 engage wire lock releases 79. As described above, this releases tension wires 36 from wire locks 80 and permits overtube to assume its most flexible state.

In accordance with one aspect of the present invention, overtube 22 of the embodiment of FIG. 9 may be replaceably removed from yoke 84 of handle 71. In addition tension wires 36 further may comprise connectors 85 that permit the tension wires to be disconnected. Such a configuration permits the overtube to be removed and discarded after a single use, while the handle may be sterilized and reused.

Yoke 84 is also configured to position overtube 22 so that longitudinal axis L of the overtube is angularly displaced from working axis W by a predetermined angle β. This arrangement prevents handle 71 from interfering with advancement of colonoscope 10 into lumen 25.

In accordance with yet another aspect of the present invention, overtube 22 includes atraumatic tip 86 that comprises a soft foam-like material. Atraumatic tip 86 not only facilitates advancement of overtube 22 in traversing tortuous anatomy, but also serves to retain the organ wall a safe distance away from the opening through which the colonoscope is reciprocated by radially expanding the organ wall in the vicinity of the tip, as described hereinbelow with respect to FIG. 14A. Accordingly, atraumatic tip 86 reduces the potential for tissue to be caught or pinched in lumen 25 when the colonoscope is manipulated.

Referring now to FIGS. 10–16, alternative tensioning mechanisms are described, in which the tensioning mechanisms may provide a fail-safe mode that reduces the risk of undesired reconfiguration of the overtube in the event of tensioning mechanism failure. When overtube 22 is in the rigid state, the following tensioning mechanisms are configured to self-equalize compressive loads applied to the multiplicity of nestable elements, so that if, e.g., a tension wire breaks, the overtube either softens into the flexible state or retains its shape-locked state.

FIG. 10A schematically depicts components of a first embodiment of an alternative tensioning mechanism having plurality of distal pulleys 87 operably coupled via proximal tension wire 88. Proximal tension wire 88 is slidably disposed within proximal pulley 89. Each tension wire 90 couples adjacent tension wire lumens 28, through respective distal pulleys 87. For example, if four tension wire lumens 28a–28d are provided, as in FIG. 10A, first tension wire 90a extends from tension wire lumen 28a to adjacent tension wire lumen 28b through first distal pulley 87a. Likewise, second tension wire 90b extends from tension wire lumen 28c to adjacent tension wire lumen 28d through second distal pulley 87b.

This configuration equalizes tension within tension wires 90, so that a proximally directed force F applied to proximal pulley 89 is distributed evenly through tension wires 90. When one of the tension wires breaks, this configuration allows overtube 22 to soften into its flexible state since the loss of tension in any of the tension wires is transmitted through the pulley system to the remaining tension wires.

It will be apparent to one of ordinary skill in the art that tension wires 90a and 90b may comprise either two separate lengths of wire, or a single length of wire that is looped backwards after traversing the distal-most nestable element 30. Furthermore, while FIG. 10A depicts tension wires 90 extending through adjacent tension wire lumens 28, the tension wires instead may extend through wire lumens disposed diametrically opposite each other, as shown in FIG. 10B. Tension wires 90 preferably are made from a superelastic material, e.g., nickel titanium alloy, but also may be made from braided stainless steel, single stainless steel wires, Kevlar, a high tensile strength monofilament thread, or combinations thereof. These materials are provided only for the sake of illustration and should in no way be construed as limiting.

In an alternative embodiment illustrated in FIG. 10C, proximal pulley 89 is eliminated, and distal pulleys 87 are fixed to each other, e.g., by welding, so that a unitary pulley manifold is formed. A proximally directed force F that is applied to the pulley manifold is distributed evenly through tension wires 90 that extend through respective distal pulleys 87 to diametrically disposed tension wire lumens 28 within overtube 22. If tension wires 90 comprise two separate lengths of wires, the risk of reconfiguration of overtube 22 is reduced if one of the wires breaks since the tension within the overtube, as defined by the unbroken tension wire, is symmetrically balanced. If the remaining tension wire breaks, the tension wire relaxes into the flexible state. If tension wires 90 comprise a single length of wire that breaks, the overtube immediately relaxes into the flexible state, thereby also reducing the risk of undesired configuration of the overtube in the event of tensioning system failure.

Furthermore, applicants have observed that the apparatus of the present invention also may comprise only one distal pulley 87 coupled to overtube 22 via a single tension wire 90 disposed through diametrically opposite tension wire lumens 28. When a proximally directed force is applied to the single distal pulley, the force is distributed through the single tension wire to impose a symmetrical compressive clamping load on overtube 22 that is sufficient to shape-lock the overtube. When tension wire 90 breaks, overtube 22 immediately softens into its flexible state, thereby reducing the risk of undesired reconfiguration of the overtube in the event of tensioning system failure.

Referring now to FIG. 11, lumen 25 and tension wires 90 within overtube 22 extend from the distal region of the apparatus, through overtube 22, and to handle 91. Within handle 91, the tension wires are slidably coupled to distal pulleys 87, which in turn are slidably coupled to proximal pulley 89. Proximal pulley 89 is coupled to and translates with slide block 92, that is keyed to travel along track 93 disposed within housing 94. Plunger 95 is mounted pivotally to slide block 92 at the proximal end and slidably disposed within plunger housing at a distal end.

Plunger housing 96 is mounted pivotally to actuator 27, illustratively hand grip 97. To bias hand grip 97 against actuation absent an externally applied force, compression spring 98 is provided concentrically disposed about plunger 95. Compression spring 98 maintains tension wires 90 in constant tension when the tensioning mechanism is actuated to impose a clamping load. Advantageously, if adjacent nestable elements shift slightly when overtube 22 is shape-locked, the proximal bias of compression spring 98 immediately advances slide block 92 in the proximal direction to maintain a relatively constant tension load within tension wires 90, thereby reducing the risk of reconfiguration of the overtube back to the flexible state that otherwise may occur absent compression spring 98.

Hand grip 27 also includes pawl 99, which is disposed to engage teeth 100 on ratchet bar 101 to prevent distally-directed motion of slide block 92. Ratchet bar 101 is pivotally mounted in housing 94 with a spring (not shown) that, with the aid of compression spring 98, biases pawl 99 against teeth 100 of ratchet bar 101, to provide a one-way ratchet effect when hand grip 97 is squeezed.

In operation, squeezing hand grip 97 causes pawl 99 to capture the next proximal-most tooth 100. This movement also provides a compressive force to compression spring 98 that is transmitted to slide block 92. The proximally-directed component of the compressive force causes slide block 92 to translate along track 93, proximally retracting tension wires 90 so that a clamping load is imposed on the nestable elements within overtube 22. Further actuation of hand grip 97 causes overtube 22 to stiffen progressively in the manner previously described.

Advantageously, proximal-most tooth 100a is disposed on ratchet bar 101 at a predetermined proximal location that permits a single actuation of hand grip 97 to completely transition overtube 22 from its flexible state to its shape-fixed state. Furthermore, as pawl 99 advances hand grip 97 closer to housing 94, the mechanical advantage of the actuation of the hand grip increases. More specifically, as hand grip 97 becomes increasingly horizontal, the proximally-directed component of the force transmitted by compression spring 98 increases in magnitude. Accordingly, more force is transmitted to increase tension within tension wires 90, and thus increase the clamping load applied to rigidize overtube 22.

When it is desired to transition overtube 22 into the flexible state, pawl 99 is released from engagement with teeth 100 by rotating ratchet bar 101 in the proximal direction. The release of the compressive load applied to compression spring 98 causes hand grip 97 to rotate in the distal direction and slide block 92 to retract in the distal direction. This sufficiently relaxes tension wires 90 so that the tension wires retain little to no tension, thereby permitting overtube 22 to assume its most flexible state.

Figure 12A:
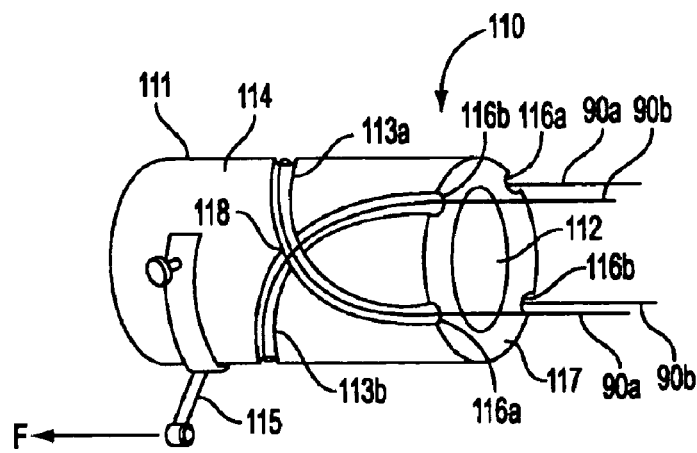
FIGS. 12A–12D are schematic perspective views of alternative components of a tensioning mechanism that each provide a fail-safe mode.

Referring now to FIGS. 12A–12D, alternative embodiments of fail-safe tensioning mechanisms are described, in which the plurality of pulleys of the previous embodiment is replaced by a single pulley manifold. In FIG. 12A, a first embodiment of a pulley manifold is described. Pulley manifold 110 includes body 111 having central bore 112 that accommodates colonoscope 10, first and second grooves 113a and 113b that each accept a tension wire, and are milled or molded into lateral surface 114 of body 111, and yoke 115 that is configured to couple pulley manifold 110 to an actuator (not shown).

First groove 113a includes a curved rack that terminates at first distal ends 116a disposed diametrically opposite each other at distal surface 117. Second groove 113b also comprises a curved track that crosses first groove 113a at intersection 118, and terminates at second distal ends 116b. Second distal ends 116b are disposed at distal surface 117 diametrically opposite each other and preferably 45o from first distal ends 116a. Similar to distal pulleys 87 of FIG. 10B, each groove accepts a tension wire that extend through diametrically disposed tension wire lumens within overtube 22. To reduce friction between tension wires 90a and 90b at intersection 118, first groove 113a may have a greater depth than that of second groove 113b, or vice versa. To prevent tension wires 90 from disengaging from grooves 113, a sleeve (not shown) may be disposed around pulley manifold 110.

If tension wires 90 comprise two separate lengths of wires, the risk of reconfiguration of overtube 22 is reduced if one of the wires breaks since the tension within the overtube, as defined by the unbroken tension wire, is symmetrically balanced. If the remaining tension wire breaks, the overtube relaxes into the flexible state. If tension wires 90 comprise a single length of wire, the overtube immediately relaxes into the flexible state if the single wire breaks. Accordingly, pulley manifold 110 provides overtube 22 with a fail-safe mode that reduces the risk of reconfiguration of the overtube in the event of tensioning mechanism failure.

Figure 12B:
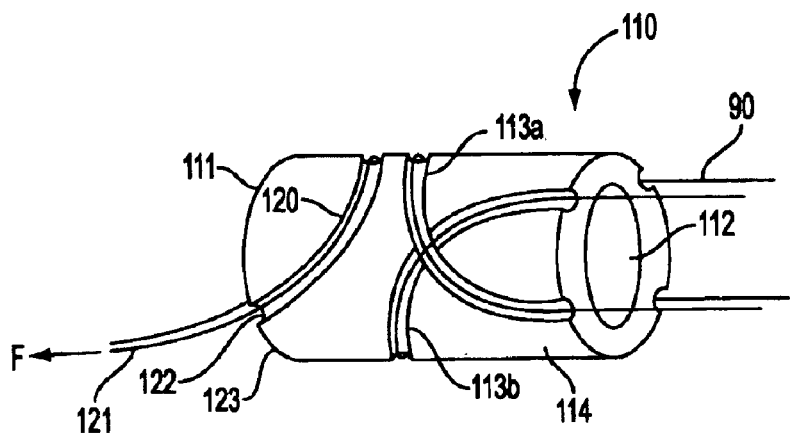

FIG. 12B depicts pulley manifold 110, in which the yoke is replaced with third groove 120. Third groove 120 is milled or molded into lateral surface 114, and accepts an additional tension wire 121 that may be coupled to actuator 27 (see FIG. 2). When a proximally directed force F is applied to tension wire 121, the force imposes tension to tension wires 90. Third groove 120 includes a curved track that terminates at third distal ends 122, which preferably are diametrically disposed opposite each other at proximal surface 123 of pulley manifold 110.

Figure 12C:
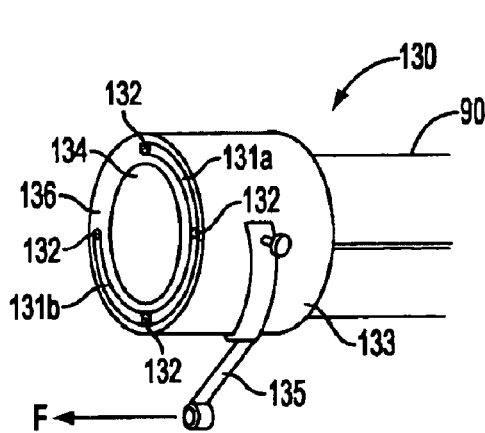
Figure 12D:
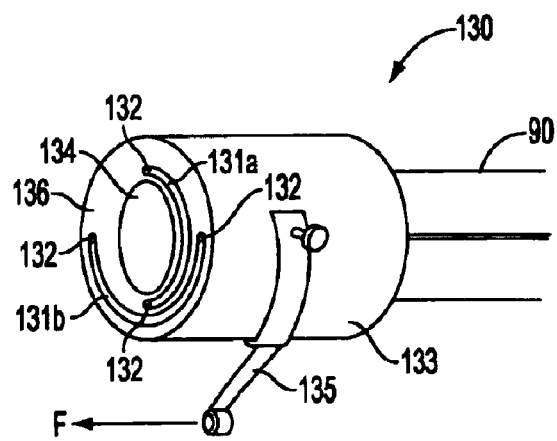

With respect to FIGS. 12C and 12D, an alternative embodiment of a pulley manifold is described. Rather than having grooves disposed on a lateral surface of the pulley manifold, pulley manifold 130 incorporates first and second grooves 131a and 131b that terminate at tension wire bores 132 disposed through body 133. Preferably, tension wire bores 132 are equidistantly and circumferentially dispose on proximal surface 136. Pulley manifold 130 also incorporates central bore 134 that accommodates colonoscope 10, and yoke 135 that couples pulley manifold 130 to actuator 27 (see FIG. 2)

In FIG. 12C, first and second grooves 131a and 131b are milled or molded in overlapping fashion. To reduce friction between tension wires disposed within the overlapping portion of the grooves, first groove 131a may have a depth greater than that of second groove 131b, or vice versa. In FIG. 12D, the first and second grooves do not overlap, first groove 131a having a smaller radius of curvature than that of second groove 131b.

Applicants also contemplate that either the first or second groove of the pulley manifolds of FIGS. 12A—12D may be eliminated so that a proximal force F applied thereto would impose a symmetrical compressive clamping force to overtube 22 through a single length of tension wire 90 that extends through diametrically disposed tension wire lumens. Accordingly, when tension wire 90 or 121 breaks, or yoke 115 fails, the overtube relaxes back into its flexible state, thereby reducing the risk of undesired reconfiguration of the overtube.

Referring now to FIGS. 13A and 13B, handle 21 is described employing pulley manifold 110 of FIG. 12B. Tension wires 90 within overtube 22, skin 45, liner (not shown for illustrative purposes) and lumen 25 extend from distal region 23 (see FIG. 2), through overtube 22, and to handle 140, which preferably measures less than or equal to 5 inches, similar to the other handle embodiments described herein. Within handle 140, tension wires are slidably coupled to pulley manifold 110, which rides within cylindrical extension 141 and cylinder 142. Cylindrical extension 141 may be integrally manufactured with housing 143, and is configured to be inserted into a patient's rectum. Concentric with cylindrical extension 141, cylinder 142 defines the proximal portion of lumen 25 disposed within handle 140.

Via additional tension wire 121, pulley manifold 110 is coupled to slide block 92, which is keyed to translate in track 93. As in handle 91 of FIG. 11, plunger 95 is coupled pivotally to slide block 92 at a proximal end, and slidably disposed within plunger housing 96 at a distal end. Concentrically disposed about plunger 95, compression spring 98 biases hand grip 97 from being actuated absent an externally applied force. As in FIG. 11, compression spring 98 maintains the level of tension within tension wires 90 if adjacent nestable elements shift slightly when overtube 22 is in the rigid state, thereby reducing the risk of reconfiguration of the overtube back to the flexible state.

Hand grip 97 also includes pawl 99, which is configured to engage tooth 144 of ratchet bar 145 to prevent distally-directed motion of slide-block 92. Tooth 144 is disposed on ratchet bar 145 at a predetermined proximal location that permits a single actuation of hand grip 97 to completely transition overtube 22 from its flexible state to its shape-fixed state. Ratchet bar 145 is mounted pivotally in housing 143 with a spring (not shown) that, with the aid of compression spring 98, biases pawl 99 against tooth 144. To release tension from tension wires 90, pawl 99 may be released from engagement with tooth 144 by rotating ratchet bar 145 in the proximal direction. This sufficiently relaxes tension wires 90 so that the tension wires retain little to no tension, thereby permitting overtube 22 to assume its most flexible state.

Handle 140 also has shield 146 coupled to a distal end thereof. Shield 146 prevents handle 140 proximal thereto from inadvertently being inserted into the patient's rectum. Handle 140 also incorporates indicator 147 (FIG. 13B) that provides a clinician with information about the rigidity of overtube 22. Indicator 147 comprises slot 148 disposed through a wall of housing 143, pointer 149 disposed through slot 148, and scale 150 disposed on an external surface of housing 143 adjacent to slot 148. Pointer 149 is coupled to translation of proximal manifold 110 so that it translates with the manifold. Scale 150 incorporates color gradations, or indicia (not shown) to indicate the rigidity of overtube 22. Of course, it will be obvious to one of ordinary skill in the art that pointer 149 may be coupled to any structure within handle 140 that moves when actuator 27 is actuated, e.g., slide block 92 or pawl 99. Alternatively, handle 140 may include a force sensor coupled between the distal end of track 93 and slide block 92.

It also will be evident to one of ordinary skill in the art that any of the handle embodiments described herein also may incorporate cylindrical extension 141 for insertion into a patient's rectum, one tooth 144 on a ratchet bar to transition the overtube from a flexible state to a rigid state with a single actuation of actuator 27, shield 146 to prevent insertion of the handle into the patient's rectum, indicator 147 to provide a clinician with information about the rigidity of the overtube, and combinations thereof.

Figure 14A:
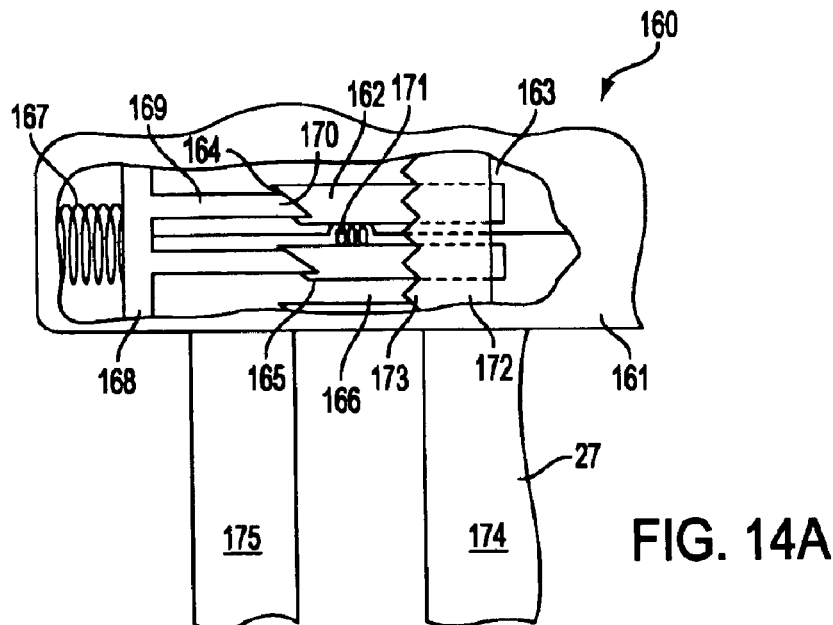
FIGS. 14A–14C are cut-away side views of an alternative tensioning mechanism that transitions the overtube of the present invention between flexible and rigid states with successive actuations.
Figure 14B:
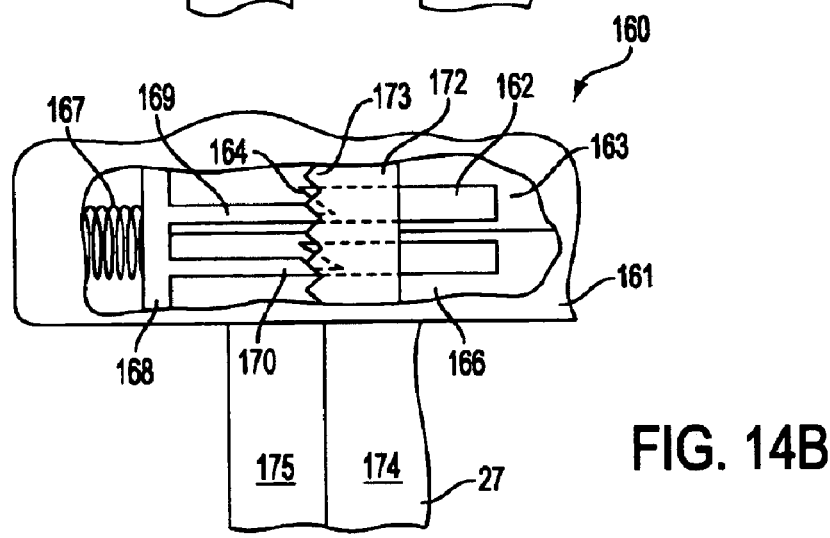
Figure 14C:
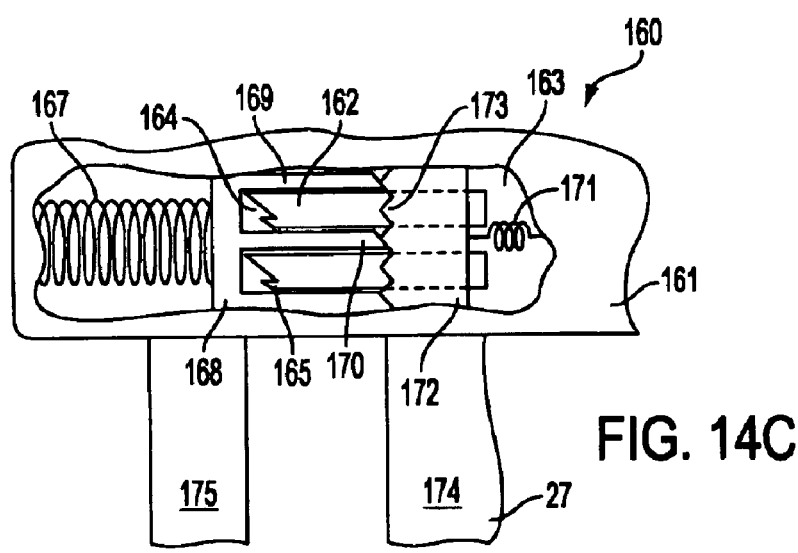

Referring now to FIGS. 14A–14C, yet another alternative embodiment of a tensioning mechanism suitable for use with the apparatus of the present invention is described. Handle 160 is adapted to reconfigure the overtube between its flexible and rigid states with successive actuations of actuator 27. Handle 160 has housing 161 containing plurality of fixed pillars 162 that are circumferentially and azimuthally disposed around inner cylindrical chamber 163 of housing 161. Each fixed pillar 162 has beveled concavity 164 disposed on a proximal end adjacent beveled arm 165. Channel 166 is disposed between adjacent pillars 162.

Handle 160 also incorporates compression spring 167 proximally disposed to bias rotatably mounted manifold 168 against plurality of pillars 162. Manifold 168 incorporates plurality of distally projecting posts 169 having beveled distal ends 170 with inclination angles that match those of beveled concavities 164 and beveled arms 165. Accordingly, when beveled distal ends 170 are forcefully engaged with beveled concavities 164, a component of the force imparted by posts 169 causes manifold 168 to rotate, absent the presence of beveled arm 165. Likewise, when the beveled distal ends are engaged with beveled arms 165, a component of the force imparted by posts 169 rotates the manifold so that pillars 162 are disposed at the proximal ends of channels 166.

Also attached to manifold 168 is tension spring 171, that in turn preferably is coupled to one of the pulley systems of FIGS. 10A–10C or 12A–12D. Tension spring 171 maintains tension wires 90 in constant tension if nestable elements disposed within the overtube slightly shift when the overtube is rigidized. Accordingly, this reduces the risk of reconfiguration of the overtube into the flexible state that otherwise would occur absent tension spring 171.

Handle 160 further comprises translatable cylindrical collar 172 having proximally projecting teeth 173. Each tooth has an inclination angle that substantially is equivalent to that of beveled distal ends 170 of manifold 168. Accordingly, when teeth 173 are engaged forcefully with beveled distal ends 170, a component of the force imparted by the teeth rotates the manifold. Also coupled to collar 172 is actuator 27, illustratively translatable hand grip 174, that may be squeezed against stationary hand grip 175 to retract collar 172 in the proximal direction to contact beveled distal ends 170 of manifold 168.

FIG. 14B depicts the configuration of handle 160 when an overtube coupled thereto is in the rigidized state. Beveled distal ends 170 of manifold 168 are engaged within concavities 164 of pillars 162. When it is desired to reconfigure the overtube into its flexible state, translatable hand grip 174 is squeezed against stationary hand grip 175. This action translates collar 172 in the proximal direction. When teeth 173 engage beveled distal ends 170, continual proximal advancement of translatable hand grip 174 causes collar to push manifold 168 in the proximal direction against compression spring 167. When beveled distal ends 170 clear beveled arm 165, the forces imparted by teeth 173 to the beveled distal ends rotate manifold 168 so that beveled distal ends 170 are engaged to beveled arms 165, as shown in FIG. 14B.

Retraction of collar 172 disengages teeth 173 from manifold 168. The forces imparted by beveled arm 165 to the beveled distal ends rotate manifold 168 until the beveled distal ends clear pillar 162. Thereafter, the bias of compression spring 167 advances plurality of posts 169 into channels 166. FIG. 14C depicts this configuration, in which the overtube is in its flexible state.

To reconfigure the overtube back into its rigid state, translatable hand grip 174 again is squeezed against stationary hand grip 175. This proximally advances collar 172 until teeth 173 contact beveled distal ends 170 of posts 169. Continual proximal actuation of translatable hand grip 174 causes collar 172 to push posts 169 out of channels 166. When beveled distal ends 170 clear pillars 162, the forces imparted by teeth 173 to beveled distal ends 170 rotate manifold 168. Distal retraction of collar 172 disengages teeth 173 from manifold 168, and the bias of compression spring 167 advances manifold 168 until beveled distal ends 170 completely engage concavities 164.

Figure 15:
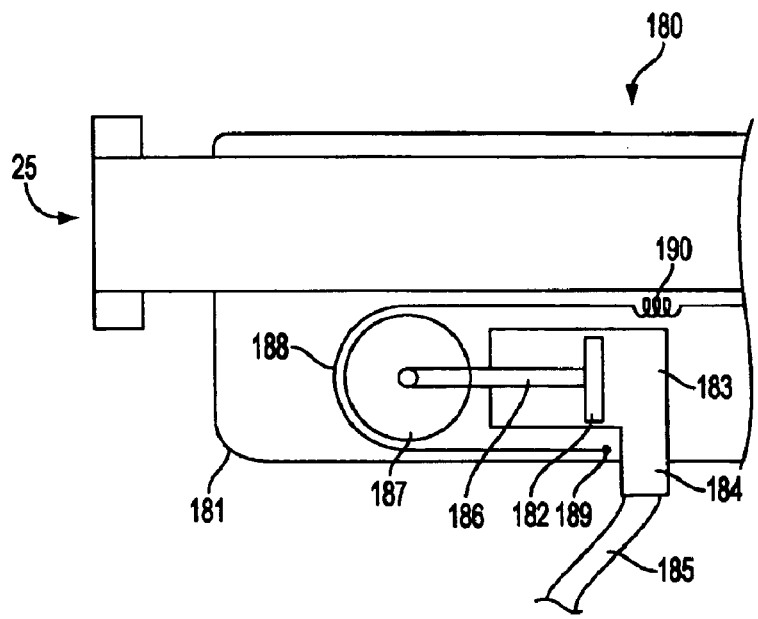
FIG. 15 is a side sectional view of yet another alternative tensioning mechanism employing pneumatic actuation.

Referring now to FIG. 15, still another alternative embodiment of handle 21 suitable for use with the apparatus of the present invention is described. Handle 180 comprises housing 181 containing lumen 25 of the overtube. Handle 180 further includes piston 182 translatably disposed within piston housing 183, which is coupled in pneumatic communication via port 184 and tube 185 with a pressure source (not shown). Attached to piston shaft 186 is pulley 187 around which proximal tension wire 188 is disposed. Proximal tension wire 188 is affixed to housing 181 at its proximal end 189 and to tension spring 190 at its distal end. Preferably, tension spring 190 distally is coupled to one of the pulley systems of FIGS. 10A–10C or 12A–12D. Similar to tension spring 171 of FIGS. 14A–14C and compression springs 98 of FIGS. 11 and 13, tension spring 190 maintains the tension wires in constant tension when the overtube is in the shape-locked state. This reduces the risk of reconfiguration of the overtube to its flexible state if nestable elements disposed therein slightly shift relative to adjacent nestable elements.

To stiffen the overtube, the pressure source may be actuated to infuse piston housing 183 with pressurized air that proximally advances piston 182. This in turn advances pulley 187 in the proximal direction, so that tension is applied to proximal tension wire 188. That tension is transmitted through tension spring 190 to tension wires disposed within the overtube, thereby imposing a compressive clamping load to adjacent nestable elements disposed within the overtube. To transition the shape-locked overtube into the flexible state, the pressure source may be actuated to remove air from piston housing 183. This retracts piston 182 and pulley 183 in the distal direction, thereby releasing the compressive clamping load applied to the overtube.

Pursuant to another aspect of the present invention, tension spring 190 may be replaced with a damper per se known in the art. In addition to the advantages provided by the tension spring, the damper allows tension within proximal tension wire 188, and thus tension wires disposed within the overtube, to be slowly released. Applicants contemplate that a damper may replace any of the compression and tension springs described herein.

Figure 16:
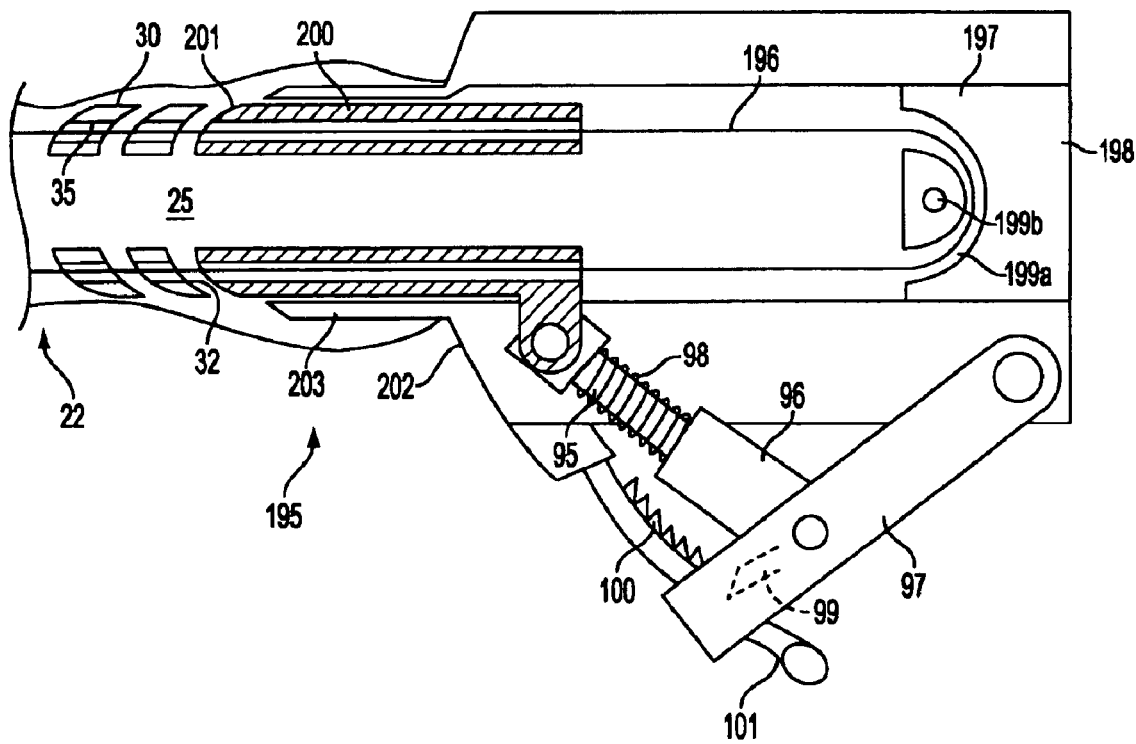
FIG. 16 is a side sectional view of a further alternative tensioning system that transitions the overtube of the present invention from a flexible state to a rigid state without substantial movement of a distal end of the overtube.

Referring now to FIG. 16, apparatus 20 may be provided with a tensioning mechanism that is selectively operable to transition overtube 22 between the flexible and rigid states substantially without proximal movement of distal region 23 (see FIG. 2). In FIG. 16, tension wire 196 and lumen 25 extend from distal region 23, through overtube 22, and to handle 195. Within handle 195, tension wire 196 is slidably coupled to pulley manifold 197 that is rigidly or rotatably affixed to distal end 198 of the handle. Pulley manifold 197 preferably includes orthogonally disposed first and second channels 199a and 199b. While FIG. 16 depicts only one tension wire, it should be understood that a second tension wire preferably is disposed through second channel 199b and nestable elements 30.

Similar to the tensioning mechanisms of FIGS. 12A–12D and 13, the present tensioning mechanism also provides overtube 22 with a fail-safe mode. If the tension wires disposed through channels 199 comprise two independent wires, the load within overtube 22 remains symmetrically distributed when one of the wires breaks. Thus, the risk of reconfiguration of overtube 22 is reduced. If these tension wires comprise a single length of wire, overtube 22 will relax into the flexible state if the single length of wire breaks.

Between pulley 197 and nestable elements 30, tension wire 196 also extends through collar 200, which has distal surface 201 that is contoured to mate with proximal surface 32 of the proximal-most nestable element 30. Collar 200 is disposed to translate within housing 202 so that distal surface 201 engages proximal surface 32 of nestable element 30 when collar 220 is advanced in the distal direction.

Collar 200 pivotally is connected to plunger 95, which is slidably disposed within plunger housing 96. Plunger housing 96 in turn is mounted pivotally to actuator 27, illustratively hand grip 97. To bias hand grip 97 against actuation absent an externally applied force, and to maintain constant tension within tension wire 196 when overtube 22 is rigidized, compression spring 98 is provided concentrically disposed about plunger 95.

Hand grip 97 also includes pawl 99, which is disposed to engage teeth 100 on ratchet bar 101 to prevent proximally-directed motion of collar 200. Ratchet bar 101 pivotally is mounted in housing 202 with a spring (not shown) that, with the aid of compression spring 98, biases pawl 99 against teeth 100 of ratchet bar 101. Handle 195 also may incorporate annular extension 203 that is disposed surrounding collar 200 and that may be inserted into a patient's rectum.

Similar in operation to handle 91 of FIG. 11, when hand grip 97 is squeezed, pawl 99 engages the next distal-most tooth 100. This action also transmits force through compression spring 98, which pushes collar 200 into engagement with the proximal-most nestable element. Continual actuation of hand grip 97 causes collar 200 to exert an increasing compressive clamping load to nestable elements 30, which causes overtube 22 to stiffen into its shape-locked state.

Advantageously, this configuration permits overtube 22 to reconfigure between the flexible and rigid states without substantial proximal movement of the distal end of the overtube. In previous embodiments, nestable elements 30 are advanced in the proximal direction when overtube 22 is rigidized, and due to compression of adjacent nestable elements, overtube 22 shortens in length. In contrast, when the present embodiment advances the nestable elements in the distal direction, overtube 22 maintains its length despite compression of adjacent nestable elements since the length of the overtube substantially is limited by the length of tension wire 196. This provides greater accuracy when using the apparatus of the present invention, and is particularly useful in delicate procedures.

It will be apparent to one of ordinary skill in the art that, similar to the tensioning mechanism described in reference to FIG. 13, ratchet bar 101 may be provided with only one tooth. Alternatively, with minor modifications that will be evident to one of ordinary skill in the art, the tensioning system of FIGS. 14A–14C may be coupled to collar 200 to transition overtube 22 between the flexible and rigid states with successive actuations of actuator 27, or the piston mechanism described in reference to FIG. 15 may be coupled to collar 200 to drive translation thereof. More specifically, rather than being pivotally coupled to plunger 95, collar 200 instead may be fixedly coupled to a piston disposed to provide motion along the longitudinal axis of collar 200. Furthermore, second channel 199b may be eliminated from pulley manifold 197 so that a single tension wire may translatably extend through first channel 199a and diametrically disposed tension wire bores disposed within collar 200 and nestable elements 30. When the single tension wire breaks, the overtube relaxes into the flexible state immediately, thereby providing a fail-safe mode that reduces the risk of undesired reconfiguration of the overtube.

With respect to FIGS. 17A and 17B, an alternative structure is described to facilitate movement of a colonoscope within lumen 25 of overtube 22. In particular, instead of using inner lining 43 as depicted in FIG. 4, some or all of nestable elements 30 may include roller bearings 205 that are received in insets 206 formed in nestable elements 30. Bearings 205 may be disposed on ring 207 to facilitate assembly of the device.

FIGS. 18A and 18B depict a further alternative embodiment, in which lubricious flexible rails 208 are disposed within bore 33 of nestable elements 30. Rails 208 span the length of lumen 25, and reduce contact between the colonoscope and the interior of the overtube, thereby facilitating movement of the colonoscope through overtube 22.

Figure 19:
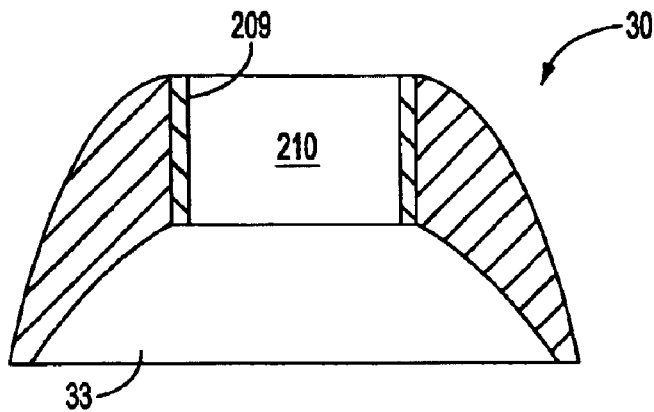
FIG. 19 is a side-sectional view of an alternative nestable element having an integral lubricious lining.

In FIGS. 19 and 20, still further alternative structures are described to facilitate movement of a colonoscope within lumen 25 of overtube 22. More specifically, rather than using liner 43 as shown in FIG. 4, some or all of nestable elements 30 may incorporate hydrophilically-coated polymeric layer 209, which may be disposed surrounding distal portion 210 of bore 33.

Figure 20A:
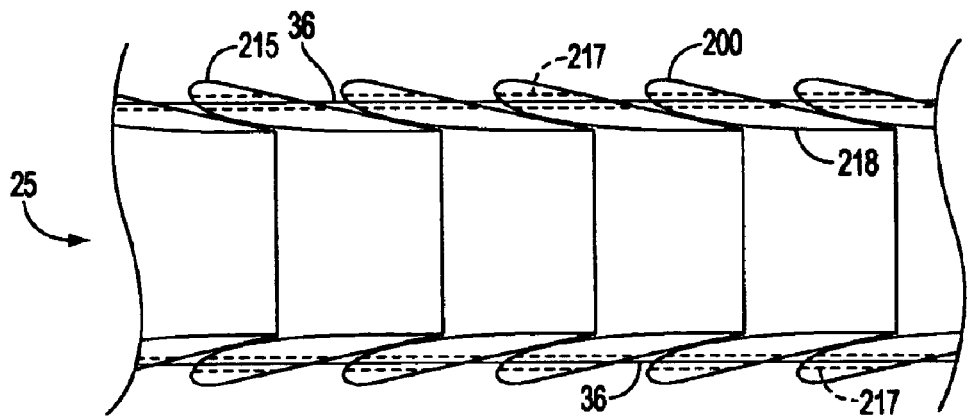
FIGS. 20A and 20B are side-sectional views of alternative nestable elements that form a smooth internal lumen when nested together.
Figure 20B:
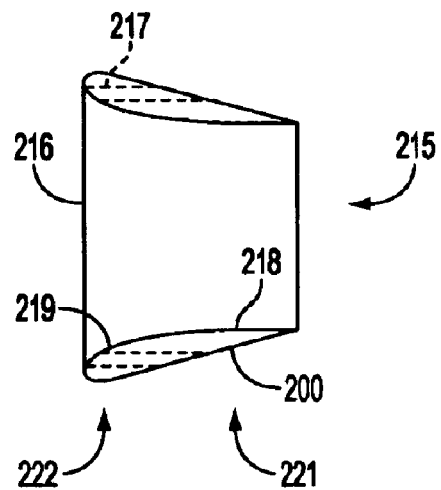

Alternatively, as described in FIGS. 20A and 20B, overtube 22 may comprise multiplicity of frustoconical elements 215 that, when nested, provide a smooth inner lumen to accommodate colonoscope 10 without the need for a separate liner. Each frustoconical element 215 includes central bore 216, and at least two or more tension wire bores 217. Central bore 216 is defined by cylindrical distal inner surface 218 that has a substantially constant diameter, and proximal inner surface 219 that is continuous with distal inner surface 218.

Proximal inner surface 219 is slightly curved in a radially outward direction so that, when tension wires 36 are relaxed, proximal inner surface 219 can rotate relative to external surface 220 of an adjacent element. External surface 220 of each frustoconical element may be straight or contoured to conform to the shape of proximal inner surface 219, and tapers each element so that distal end 221 is smaller in outer diameter than proximal end 222. When frustoconical elements 215 are nested together, distal inner surface 218 of each frustoconical element is disposed adjacent to the distal inner surface of an adjoining frustoconical element.

Advantageously, the present configuration provides lumen 25 with a substantially continuous profile. This permits smooth advancement of colonoscope 10 therethrough, and thereby eliminates the need to dispose a separate liner within lumen 25. To provide a lubricious passageway to further facilitate advancement of the colonoscope, each frustoconical element optionally may incorporate an integral hydrophilic polymeric lining as described with respect to the preceding embodiment of FIG. 19, or a thin, flexible lining having a hydrophilic coating may be disposed through lumen 25.

Figure 21A:
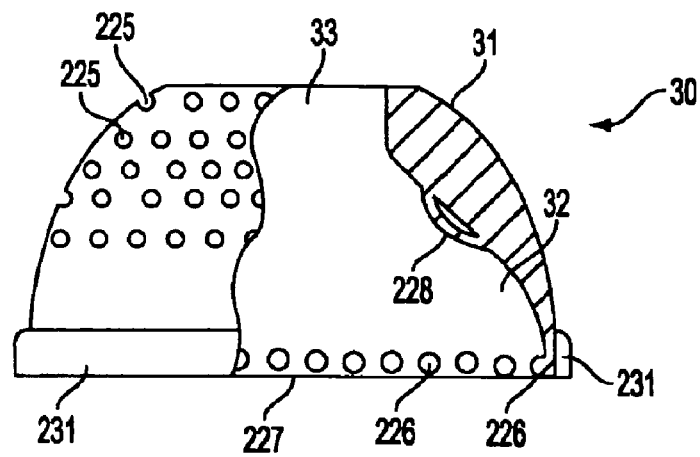
FIGS. 21A–21D are still further alternative embodiments of the nestable elements of FIG. 3, in which the nestable elements are macroscopically textured to enhance friction.
Figure 21B:
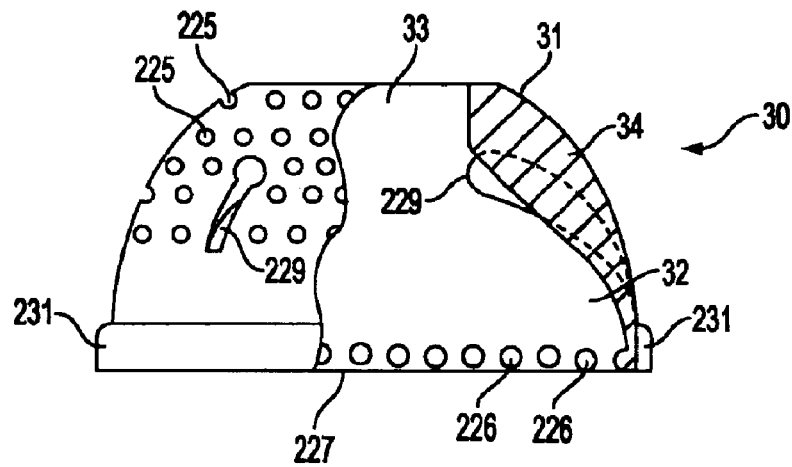
Figure 21C:
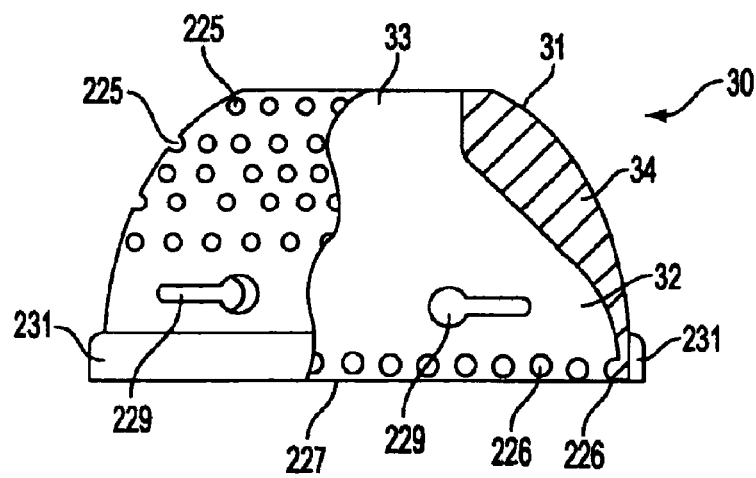

In FIGS. 21A–21C, yet another alternative structure is described, in which distal surface 31 of each nestable element is macroscopically textured to increase the friction between adjacent nestable elements 30 when a compressive clamping load is applied to overtube 22. Illustratively, each element 30 may incorporate multiplicity of divots 225 disposed on distal surface 31, and teeth 226 that are disposed on proximal surface 32 adjacent proximal edge 227. Teeth 226 are contoured to mate with the multiplicity of divots disposed on an adjacent element. Accordingly, when overtube 22 is tensioned, retraction of tension wires 36 (see FIG. 3) applies a clamping load to elements 30 that causes teeth 226 of each element to forcefully engage divots 225 of an adjacent element. This reduces the risk of relative angular movement between adjacent nestable elements 30 when overtube 22 is shape-locked, which in turn reduces the risk of undesired reconfiguration of the overtube.

To prevent divots 225 and teeth 226 from engaging, and thus provide smooth angular movement between adjacent elements 30, when overtube 22 is in the flexible state, one or more leaf springs 228 may be molded integrally with proximal surface 32. Accordingly, absent compressive clamping load applied by tension wires 36 to stiffen overtube 22, leaf spring 228 of each element 30 coacts with distal surface 31 of an adjacent element to prevent coaction of proximal and distal surface 32 and 31, which prevents engagement of teeth 226 with divots 225.

Alternatively, rather than having a leaf spring, nestable elements 30 may be provided with one or more cantilever springs 229 that are cut from wall 34 and plastically bent into bore 33 of nestable element 30. Similar to leaf springs 228, cantilever springs 229 prevent coaction between distal and proximal surfaces 31 and 32 so that teeth 226 do not engage divots 225 absent a compressive clamping load. Cantilever springs 229 may be aligned with a longitudinal axis of nestable element 30, as shown in FIG. 21B, and/or aligned with a circumference of nestable element 30, as shown in FIG. 21C. Applicants also contemplate that teeth 226 may be disposed on distal surface 31 and divots 225 may be disposed on proximal surface 32. One of ordinary skill in the art will recognize additional macroscopic textures that will increase friction between distal and proximal surfaces of adjacent elements 30.

Figure 21D:
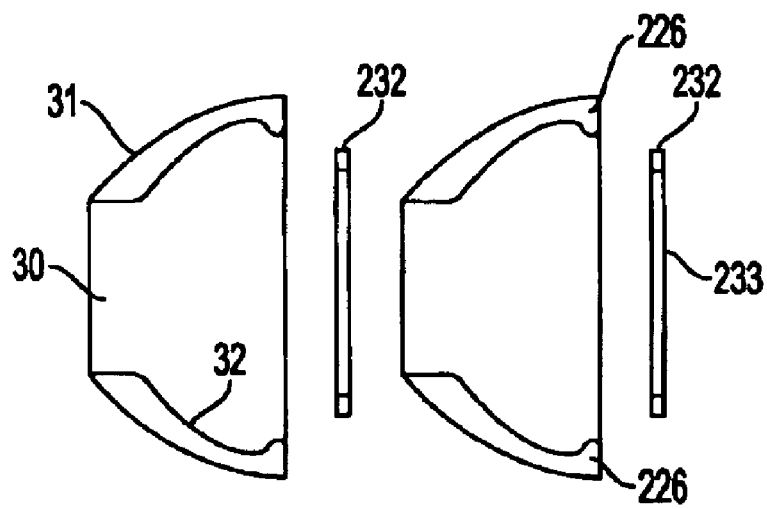

On the other hand, instead of providing leaf or cantilever springs integral with nestable elements 30, thin, flexible disc 232 (FIG. 21D) may be disposed between adjacent nestable elements 30 to prevent divots 225 (see FIGS. 21A–21C) and teeth 226 of the adjacent elements from engaging, absent a compressive clamping load. Each disc 232 incorporates central bore 233 that accommodates a colonoscope, and is made from an elastomeric material. For purposes of illustration, nestable elements 30 and discs 232 are shown spaced-apart, but it should be understood that the elements and discs are disposed so that distal surface 31 of one element 30 and proximal surface 32 of an adjacent element coacts with disc 232, which is disposed therebetween. It also should be understood that each nestable element 30 also comprises tension wire bores, which are not shown in FIGS. 21A–21D for illustrative purposes.

Pursuant to one aspect of the present invention, nestable elements 30 also may incorporate band 231 that is disposed distally adjacent to proximal edge 227. Band 231 increases the thickness of the proximal portion of wall 34 to distribute the applied compressive clamping load over a larger cross-sectional area, and thereby reduce radially outward deflection of wall 34. This in turn reduces longitudinal contraction of overtube 22. Band 231 preferably is made from a metal to provide greater structural integrity to wall 34, but also may be integral therewith.

Figure 22:
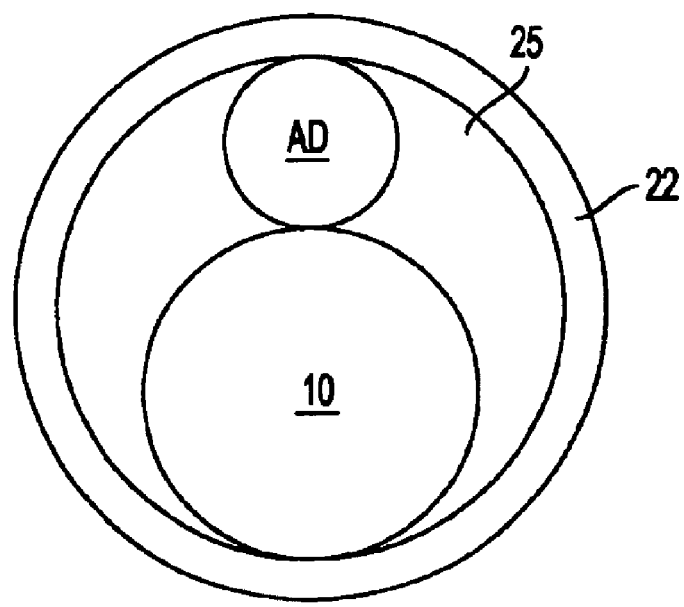
FIG. 22 is a schematic view of the lumen of the overtube of the present invention depicting the use of multiple devices.

In accordance with another aspect of the present invention, the diameter of lumen 25 preferably is configured to facilitate simultaneous passage of more than one diagnostic or therapeutic instrument therethrough. As shown in FIG. 22, lumen 25 may be dimensioned to permit auxiliary devices AD, such as for aspiration, biopsy, or additional lighting, to be advanced alongside colonoscope 10. For example, if lumen 25 has a diameter of 13 mm and colonoscope 10 has an outer diameter of 10 mm, auxiliary device AD, such as a catheter, having a diameter of between 3F to 9F may be advanced through the remaining space within lumen 25. Advantageously, this permits auxiliary devices AD to be successively placed within the patient's colon to perform additional diagnostic or therapeutic procedures without the need to remove colonoscope 10 and overtube 22 therefrom.

Figure 23:
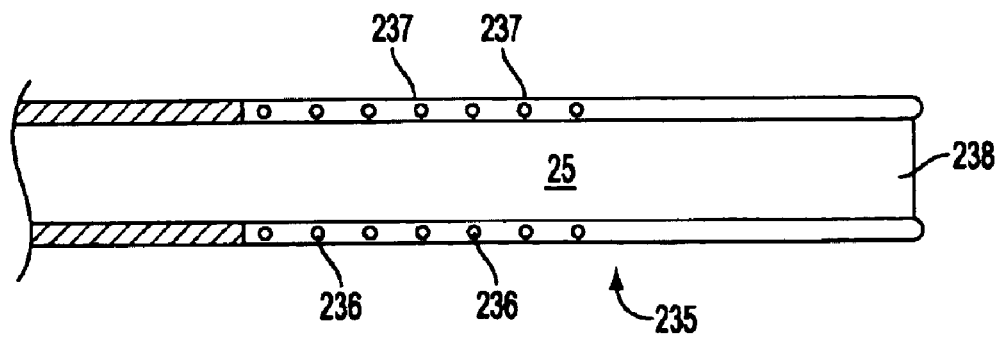
FIGS. 23–28 depict side-sectional views of various alternative embodiments of an atraumatic tip constructed in accordance with the present invention.

Referring to FIG. 23, an alternative embodiment of a distal region suitable for use in the overtube of the present invention is described. Distal region 235 is similar in construction to distal region 23 of the embodiment of FIG. 4, but has flexible coil 236 embedded in only the proximal portion of elastomeric layer 237. Atraumatic tip 238 at the distal end of distal region 235 may further enhance the steerability of overtube 22 when the steerable tip of the colonoscope is disposed therein.

FIGS. 24–28 illustrate additional configurations of atraumatic tips suitable for causing "tenting" of the wall of the hollow body organ. As used herein, tenting refers to the tendency of the atraumatic tip to be deflected radially outward in the vicinity of the tip of the overtube. This reduces the risk that the wall of the organ will become pinched or caught between the colonoscope and the entry to overtube 22 when the colonoscope is retracted within the overtube.

Figure 24A:
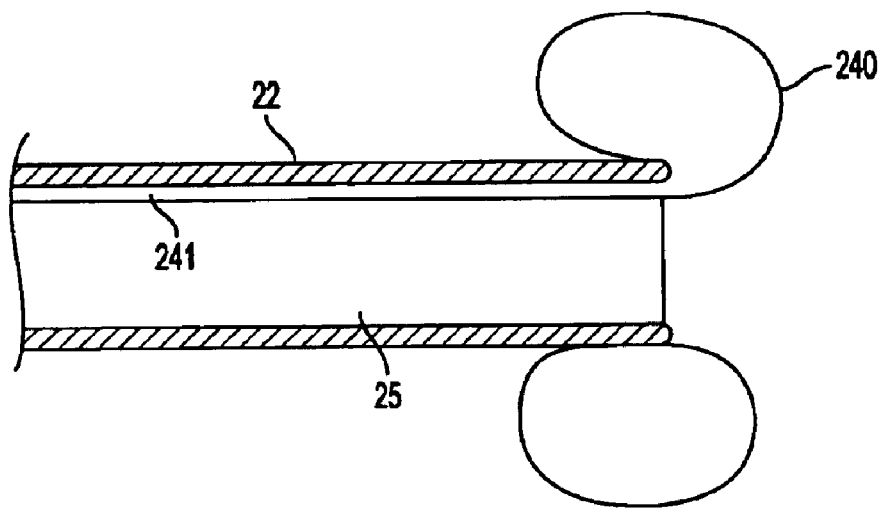
Figure 24B:
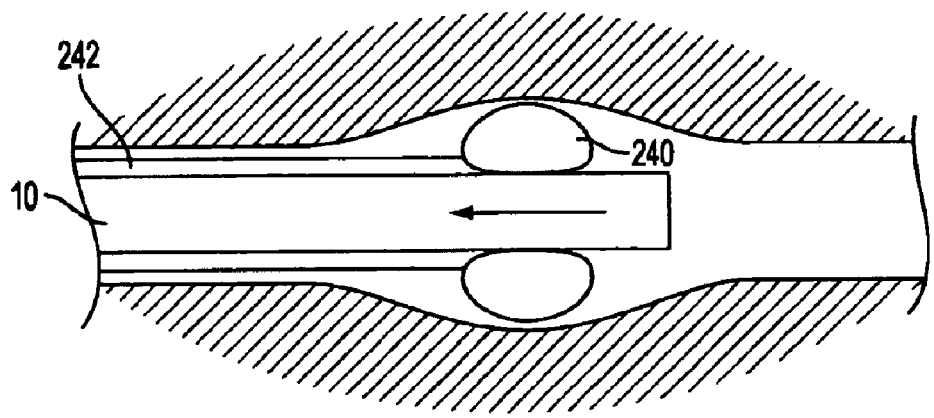

FIG. 24A shows atraumatic tip 24 in the form of an inflatable donut-shaped balloon 240 affixed to distal region 23 of overtube 22. Inflation lumen 241 extends from the handle through overtube 22 to provide fluid communication between balloon 240 and an inflation source, such as a syringe (not shown). As illustrated in FIG. 24B, when balloon 240 is inflated, the wall of the colon radially deflects around balloon 240. Thus, when colonoscope 10 is retracted into lumen 25, it is less likely that the wall of the colon will be pinched or potentially dissected between overtube 22 and colonoscope 10. Furthermore, when inflated, balloon 240 closes annular gap 242 disposed between the wall of overtube 22 and colonoscope 10 to prevent bodily fluids and other matter from entering lumen 25. Advantageously, balloon 240 provides a custom fit around colonoscope 10.

Figure 25:
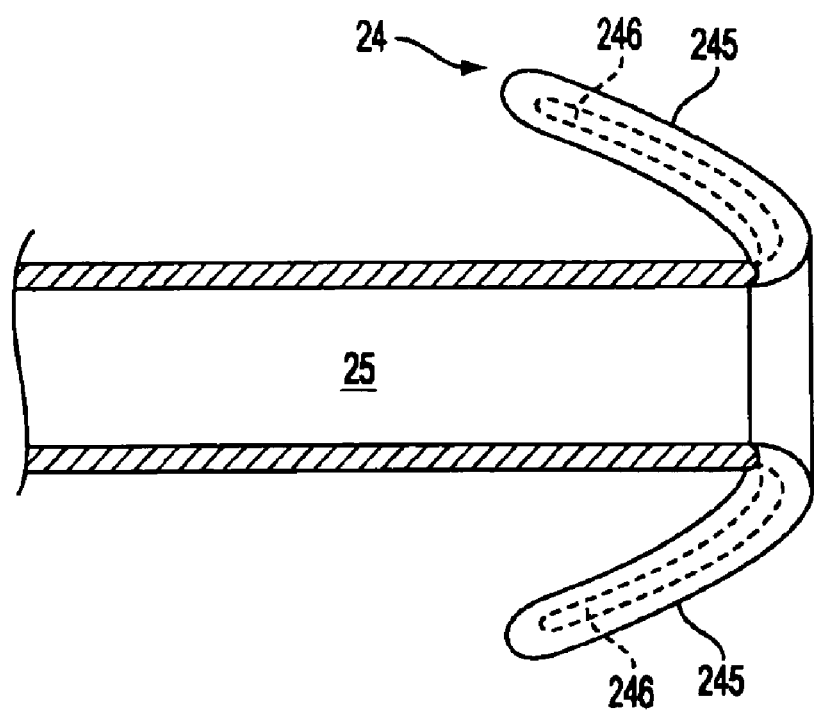

FIG. 25 depicts a further alternative embodiment of atraumatic tip 24, comprising soft membrane 245 covering shape memory alloy petals 246. Petals 246 preferably comprise loops of shape memory alloy wire, e.g., nickel titanium alloy, and extend radially outward in the proximal direction near the distal opening into lumen 25, so that the proximal end of membrane-covered petals causes the "tenting" effect described hereinabove. The shape memory alloy may be activated to adopt a preformed shape when exposed to body temperature, and returned to a contracted state by flushing overtube 22 with cold water or air. Alternatively, petals 246 may be mechanically extended or retracted, or self-expanding.

Figure 26:
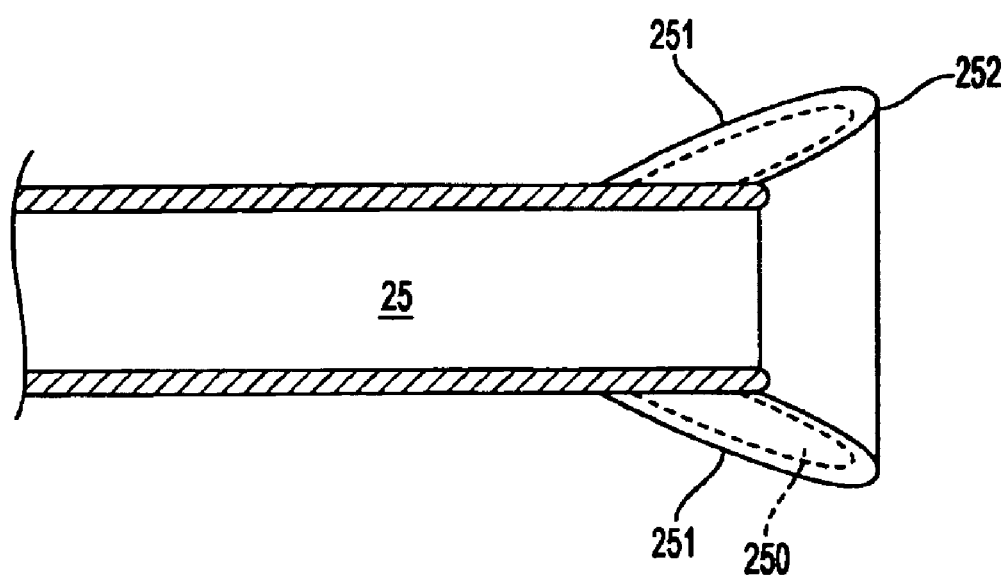

FIG. 26 depicts a further alternative embodiment of atraumatic tip 24. In the embodiment of FIG. 26, petals 250 covered by soft elastomeric membrane 251 extend distally from distal region 23 to form funnel-shaped element 252. Atraumatic tip 24 provides a similar tenting effect to that described for the preceding embodiments.

Figure 27:
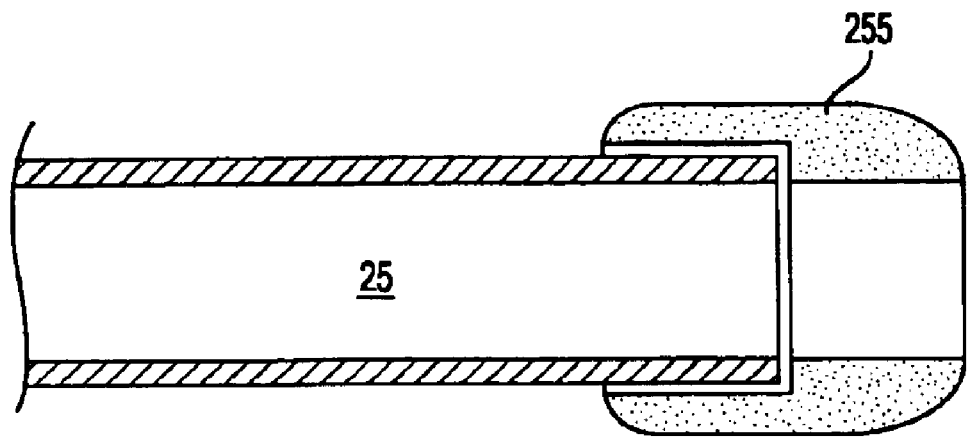
Figure 28:
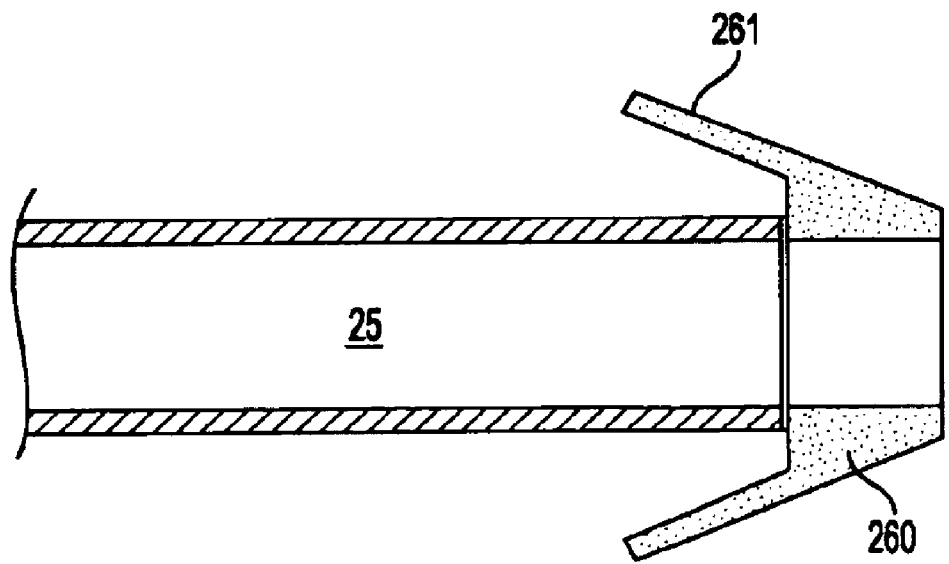

FIGS. 27–28 provide further alternative configurations for atraumatic tip 86 of the embodiment of FIG. 9. Tip 255 preferably comprises a foam or soft elastomer, and may be affixed to distal region 23 of overtube 22 using a suitable biocompatible adhesive. FIG. 28 depicts an alternative shape for a foam or soft elastomer bumper 260, which includes a proximally-extending flange 261. Of course, one of ordinary skill in the art will recognize that other configurations may be used in accordance with the principles of the present invention to form atraumatic tips that cause localized tenting of the colon wall, and these atraumatic tips may be used with the passively-steerable distal regions of the embodiments of FIGS. 4 and 23.

Figure 29:
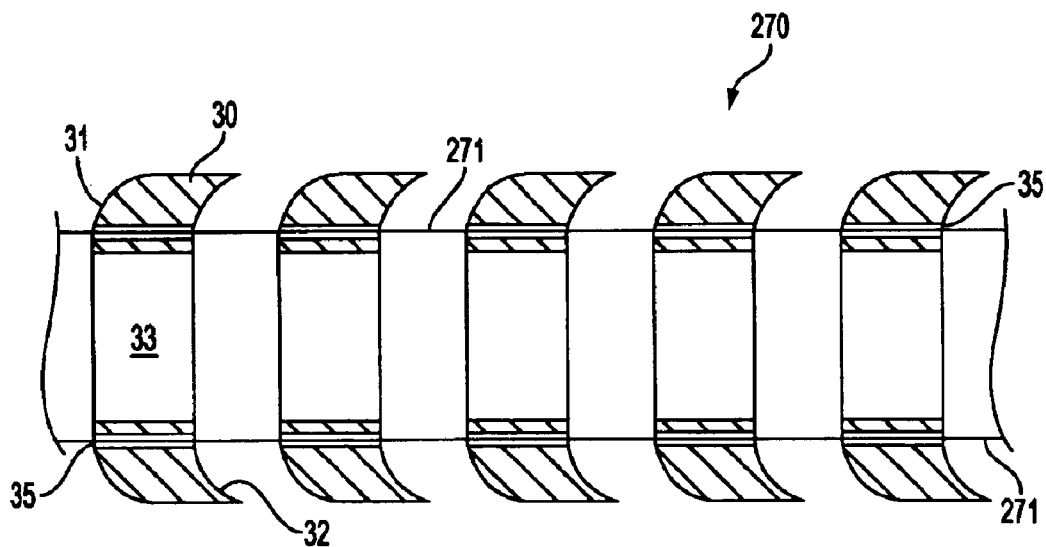
FIGS. 29 and 30 are alternative embodiments of the overtube of the present invention, having tensioning systems that employ shape memory materials.
Figure 30:
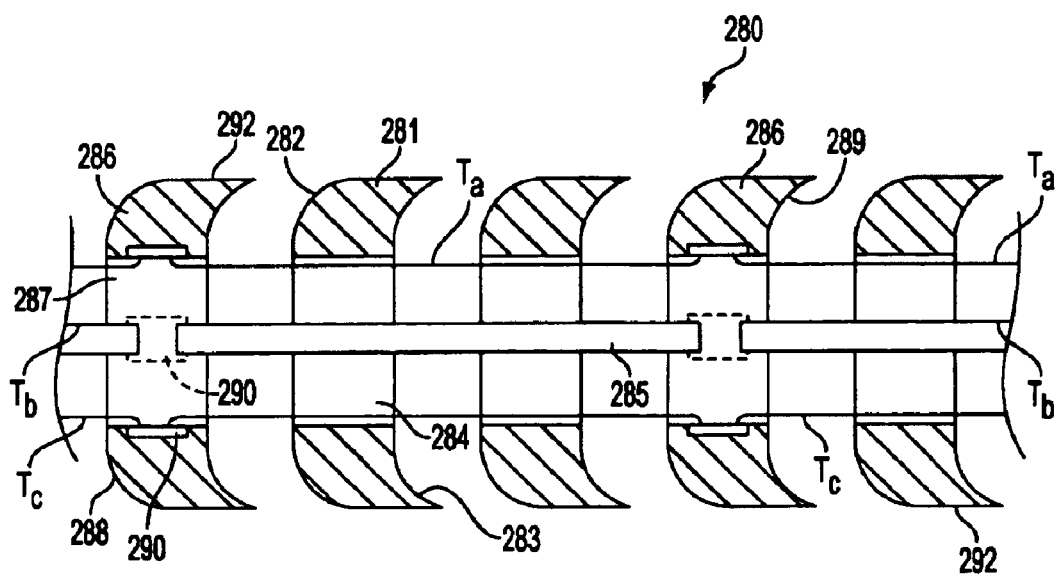

Referring now to FIGS. 29 and 30, alternative embodiments of the overtube are described. Unlike overtube 22 of previously described embodiments, in which a mechanical mechanism is actuated to impart a clamping load to a multiplicity of nestable elements, the embodiments of FIGS. 29 and 30 use alternative tensioning mechanisms. In particular, the following embodiments comprise a multiplicity of links to which a compressive clamping load may be applied by contraction of shape memory materials.

In FIG. 29, a first alternative embodiment of the overtube of the present invention is described. Overtube 270 includes multiplicity of nestable elements 30 identical to those described hereinabove. For purposes of illustration, nestable elements 30 are shown spaced-apart, but it should be understood that elements 30 are disposed so that distal surface 31 of each element 30 coacts with proximal surface 32 of an adjacent element. Each of nestable elements 30 has central bore 33 to accommodate colonoscope 10, and preferably two or more tension wire bores 35. When assembled as shown in FIG. 29, nestable elements 30 are fastened with distal and proximal surfaces 31 and 32 disposed in a coacting fashion by a plurality of tension wires 271 that extend through tension wire bores 35.

In contrast to overtube 22 of the previous embodiments, tension wires 271 of the present overtube are made from a shape memory material, e.g., nickel titanium alloy or an electroactive polymer known in the art. Tension wires 271 are fixedly connected to the distal end of overtube 270 at the distal ends and fixedly connected to handle 21 at the proximal ends. When an electric current is passed through tension wires 271, the wires contract in length, imposing a compressive clamping load that clamps distal and proximal surfaces 31 and 32 of nestable elements 30 together at the current relative orientation, thereby fixing the shape of overtube 270. When application of electrical energy ceases, tension wires 271 re-elongates in length to provide for relative angular movement between nestable elements 30. This in turn renders overtube 270 sufficiently flexible to negotiate a tortuous path through the colon.

To provide overtube 270 with a fail-safe mode that reduces the risk of undesired reconfiguration of the overtube in the event of tensioning mechanism failure, diametrically disposed tension wires 271 may be coupled in a serial circuit. Accordingly, when one wire fails, the wire disposed diametrically opposite also re-elongates to maintain a symmetrical clamping load within overtube 270. Alternatively, all tension wires 271 may be electrically coupled in a serial electrical circuit. Accordingly, when one of the tension wires fails, overtube 270 returns to the flexible state.

It should be understood that a tension spring (not shown) or damper (not shown) that are similar to those described hereinabove may be coupled between the proximal ends of tension wires 271 and handle 21 (see FIG. 2). Inter alia, this maintains the tension wires in constant tension when the overtube is in the shape-locked state, thereby reducing the risk of reconfiguration of the overtube to its flexible state if nestable elements disposed therein slightly shift relative to adjacent nestable elements.

Alternatively, as described in FIG. 30, overtube 280 may include multiplicity of nestable elements 281 that are similar to those of the preceding embodiments. For purposes of illustration, nestable elements 281 are shown spaced-apart, but it should be understood that elements 281 are disposed so that distal surface 282 of each element 280 coacts with proximal surface 283 of an adjacent element. Each of nestable elements 280 has central bore 284 to accommodate colonoscope 10.

When assembled as shown in FIG. 30, nestable elements 280 are fastened with distal and proximal surfaces 282 and 283 disposed in coacting fashion by plurality of thin tension ribbons 285 that are fixedly connected to nestable bridge elements 286. Tension ribbons 285 are made from a shape memory material, e.g., nickel titanium alloy or an electro-active polymer, and may be transitioned from an equilibrium length to a contracted length when electrical current is passed therethrough.

Nestable bridge elements 286 are disposed within overtube 280 between a predetermined number of nestable elements 281. Similar to nestable elements 281, bridge elements 286 also comprise central bore 287 that accommodates colonoscope 10, distal surface 288 that coacts with proximal surface 283 of a distally adjacent nestable element, and proximal surface 289 that coacts with distal surface 282 of a proximally adjacent nestable element 281. Each bridge element also incorporates plurality of conductive elements 290 that are disposed azimuthally around central bore 287, and that preferably couple tension ribbons 285 occupying the same angular circumferential position within overtube 280 in a serial electrical circuit.

When an electrical current is passed through tension ribbons 285, the ribbons contract in length, imposing a compressive load that clamps distal and proximal surfaces of adjacent nestable elements together at the current relative orientation, thereby fixing the shape of overtube 280. When the energy source ceases providing electricity, tension ribbons 285 re-elongates to the equilibrium length to provide for relative angular movement between the nestable elements. This in turn renders overtube 280 sufficiently flexible to negotiate a tortuous path through the colon.

Pursuant to another aspect of the present invention, tension ribbons 285 that are disposed at diametrically opposite circumferential positions may be electrically coupled in a serial circuit.

Advantageously, this configuration provides overtube 280 with a fail-safe mode that reduces the risk of undesired reconfiguration of the overtube in the event that one of the electrical circuits established through the tension ribbons is de-energized.

For example, overtube 280 of FIG. 30 may be provided with four sets of tension ribbons equidistantly disposed at 90° intervals. In the event that tension ribbons $T_a$ de-energize, absent electrical communication between tension ribbons $T_a$ and tension ribbons $T_c$ disposed diametrically opposite thereto, overtube 280 will spontaneously reconfigure into a new rigidized shape since the tension within the overtube no longer will be symmetrically balanced. The new shape of overtube 280 may not replicate the tortuous path of the colon, and thus may cause substantial harm to the patient.

Advantageously, the present invention may reduce the risk of undesired reconfiguration preferably by electrically coupling diametrically disposed tension ribbons in a serial circuit. When tension ribbons $T_a$ are de-energized, tension ribbons $T_c$ also de-energize to provide overtube 280 with symmetrical tension, as provided by tension wires $T_b$ and the tension wires disposed diametrically opposite thereto (not shown). In this manner, the overtube retains its desired rigidized shape in the event that the tensioning mechanism malfunctions. To immediately return overtube 280 to its flexible state in the event that any of the tension ribbons are de-energized, all tension ribbons 285 may be electrically coupled in a serial circuit.

In an alternative embodiment, tension ribbons 285 may be electrically coupled to rigidize select regions of the overtube without rigidizing the remainder of the overtube. Illustratively, this may be accomplished by coupling longitudinally adjacent tension ribbons in a parallel circuit, and circumferentially adjacent tension ribbons in a serial circuit.

Of course, it will be evident to one of ordinary skill in the art that, while FIG. 30 depicts tension ribbons 285 to be disposed within central bores 284 and 287, the tension ribbons also may be disposed adjacent external lateral surfaces 292 of nestable elements 281 and 286. Alternatively, the tension ribbons may extend through tension ribbon bores (not shown) that may extend through the distal and proximal surfaces of nestable elements 281, and be affixed to nestable bridge elements 286.

With respect to FIGS. 31–37, alternative embodiments of overtube 22 are described. Unlike overtube 22 of the above-described embodiments, which comprised a multiplicity of nestable elements that are clamped with a plurality of tension wires or ribbons, the embodiments of FIGS. 31–37 use alternative clamping mechanisms. In particular, the following embodiments comprise a plurality of links that may be stiffened by the use of compressive sleeves that compress individual links disposed along the length of the overtube.

Figure 31A:
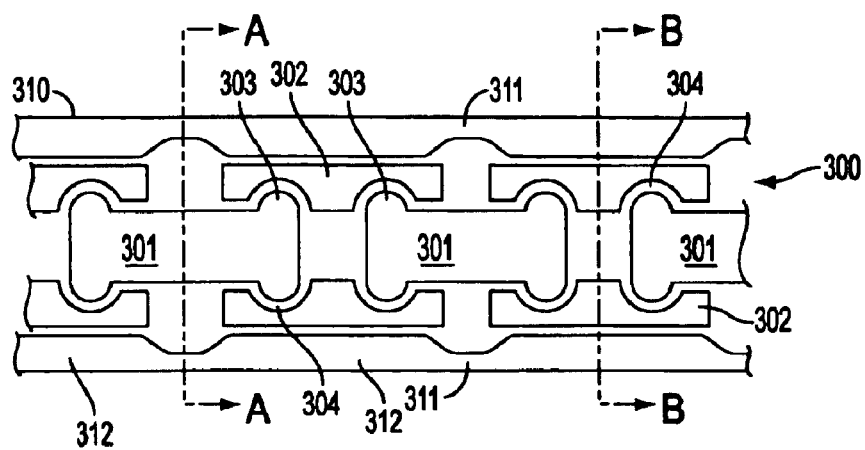
FIGS. 31A–31C are, respectively, a side-sectional view of an alternative embodiment of an overtube suitable for use in the present invention having a multiplicity of interconnected links surrounded by a clamping sleeve, and cross-sectional views of portions of the sleeve.
Figure 31B:
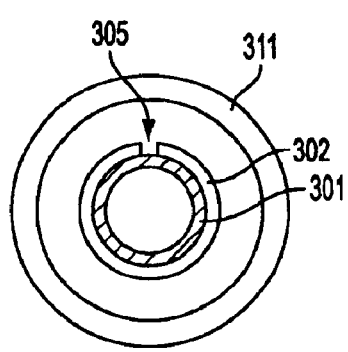
Figure 31C:
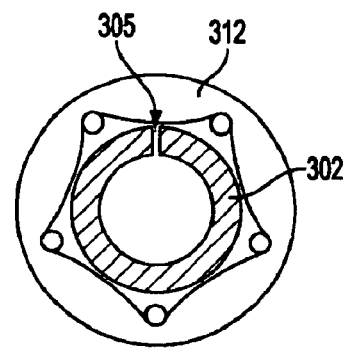

Referring now to FIGS. 31A–31C, a fourth alternative embodiment of the overtube of the present invention is described. Overtube 300 comprises a multiplicity of alternating spool links 301 and clamp links 302. Each spool link 301 and clamp link 302 has a bore disposed therethrough to accommodate a standard colonoscope. Spool link 301 comprises rounded edges 303 disposed on its distal and proximal ends that are contoured to permit limited rotatable engagement with one of two contoured grooves 304 disposed within the bore of clamp link 302. Accordingly, clamp link 302 comprises a greater outer diameter than spool link 301. Each clamp link 302 also has through-wall split 305 longitudinally disposed to permit a reduction in the diameter of clamp link 302 when the clamp link is compressed, as discussed hereinafter.

Still referring to FIGS. 31A–31C, a first embodiment of a compressive sleeve comprising inflatable sleeve 310 having first compressive portions 311 and second compressive portions 312. Sleeve 310 is configured so that the inner diameters of second compressive portions 312 are smaller than those of first compressive portions 311 when sleeve 310 is inflated. Second compressive portions 312 may be disposed to engage clamp links 302. Thus, when inflatable sleeve 310 is inflated by an inflation source (not shown) coupled to the handle, second compressive portions 312 compress against clamp links 202 to shape-fix overtube 300. In FIGS. 31B and 31C, cross sectional views of first compressive portions 311 and second compressive portions 312, respectively, are shown when sleeve 310 is in its inflated state.

Figure 32:
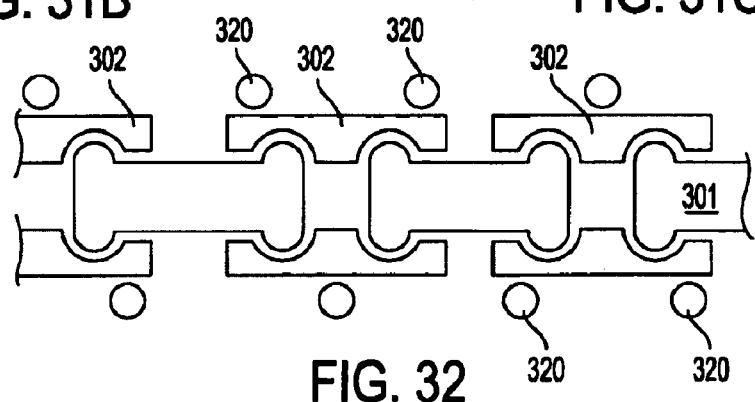
FIG. 32 is a side-sectional view of a further alternative embodiment of an overtube constructed in accordance with the present invention having a spiral bladder to actuate the clamping links.

FIG. 32 illustrates an alternative embodiment of a compressive sleeve that also comprises an inflatable bladder. Unlike inflatable bladder 310 of FIGS. 31A–31C, spiral bladder 320 has a constant inner diameter. Spiral bladder 320 preferably is helically disposed around the overtube. Accordingly, when bladder 320 is inflated, clamp links 302 are compressed onto spool links 301 to stiffen the overtube.

Figure 33:
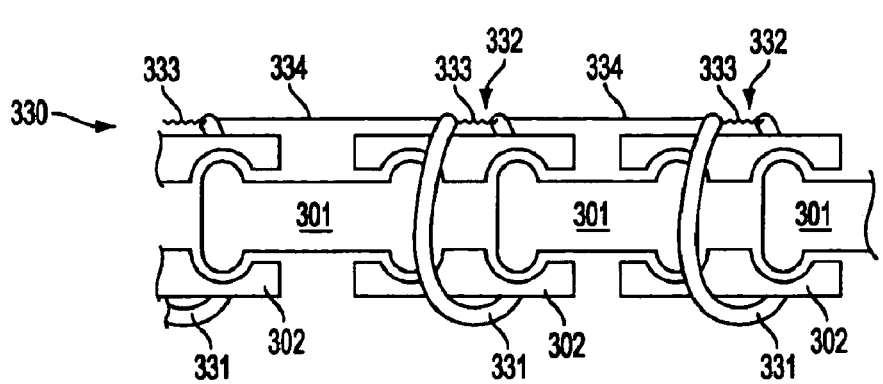
FIG. 33 is a side-sectional view of another alternative embodiment of an overtube of the present invention having thermally-actuable bands.

FIG. 33 depicts a further embodiment of a compressive sleeve 330, comprising discontinuous hoops 331 made of shape memory alloy (e.g. nickel titanium alloy). Each hoop 331 includes gap 332, which is spanned by spring 333. Each hoop 331 is electrically connected to neighboring hoops 331 via insulated wires 334, so that a serial electrical circuit is established. When hoops 331 are energized, they undergo a phase transition that causes the hoops to contract into a preformed shape that is diametrically smaller than the non-energized shape. Since hoops 331 may be disposed about clamp links 302, contraction of hoops 331 may be used to apply a clamping load that compresses links 302 onto spool links 301 to stiffen the overtube.

Springs 333 contribute to structural integrity when hoops 331 are in their non-energized state. To energize and thereby contract hoops 331, an electrical current may be run through wires 334. To return hoops 331 to their non-contracted state and thereby return the overtube to its flexible state, hoops 331 may be flushed with cold water or air. Of course one of ordinary skill in the art will recognize that hoops 331 also may be individually energized, thus requiring a parallel circuit.

Figure 34A:
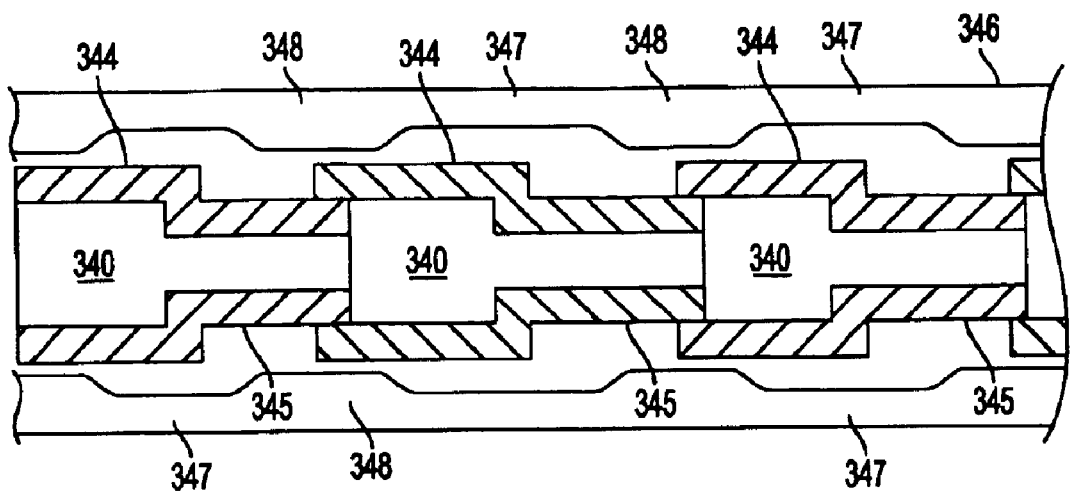
FIGS. 34A and 34B are side-sectional views of a yet further alternative embodiment of an overtube of the present invention comprising a series of helical links having regions of different durometer.
Figure 34B:
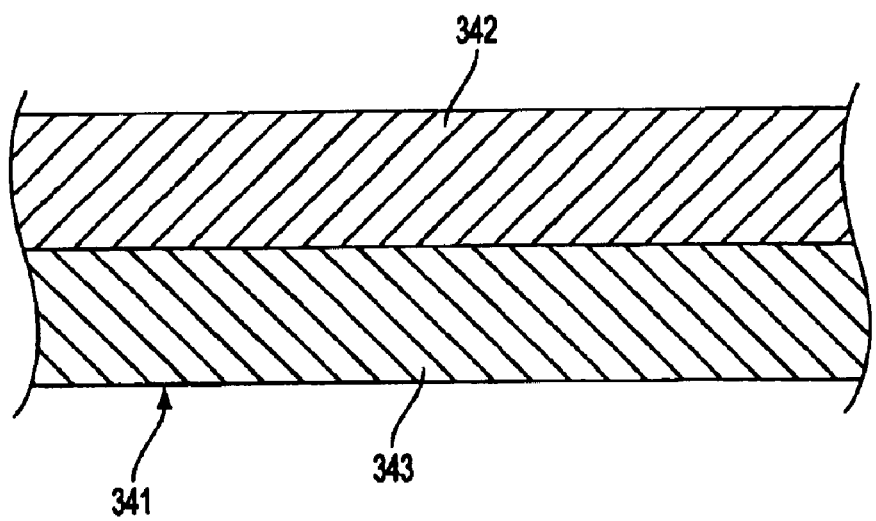

With respect to FIGS. 34A–34B, a still further alternative embodiment of an overtube suitable for use in the present invention is described. This embodiment comprises helical links 340 that are formed from an integral strip 341 having regions of different durometer, e.g., rigid material 342 and soft material 343. When strip 341 is helically wound, helical links 340 are formed having rigid portions 344 and soft portions 345. Rigid portions 344 provide structural integrity to the overtube, while soft portions 345 provide flexibility.

Helical links 340 are disposed within compressive sleeve 346, which includes first compressive portions 347 and second compressive portions 348. Compressive sleeve 346 is identical in structure and operation to that described in FIGS. 31A–31C, except that second compressive portions 348 are aligned with, and apply a clamping force to, rigid portions 344 of helical links 340. It will of course be understood that an overtube in accordance with the principles of the present invention could alternatively be formed using helical links 340 and either of the clamping systems described with respect to FIGS. 32 and 33.

Figure 35:
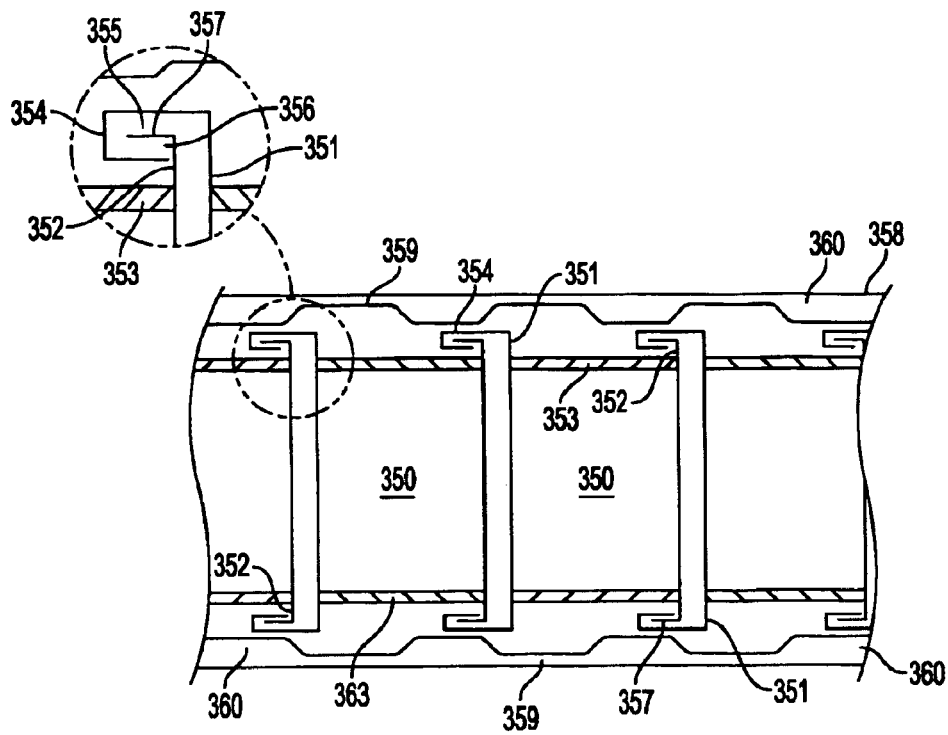
FIG. 35 is a side-sectional view of a still further alternative embodiment of an overtube suitable for use with the present invention comprising a series of links having proximal and distal rims that interlock.

Referring now to FIG. 35, another alternative embodiment of an overtube is described, in which each Grecian link 350 includes rigid first and second rims 351 and 352 disposed at longitudinally opposing ends of flexible body 353. First rim 351 comprises U-shaped arm 354 that defines channel 355 and opening 356. Second rim 352 includes retroflexed arm 357, which when engaged to first rim 351 of an adjacent, is disposed within channel 355 of U-shaped arm 354 through opening 356 so that U-shaped arm 354 and retroflexed arm 357 are engaged and overlap along the longitudinal axis of the overtube.

Grecian links 350 are disposed within compressive sleeve 358, which includes first compressive portions 359 and second compressive portions 360. Compressive sleeve 358 is identical in structure and operation to that described in FIGS. 31A and 34A, except that second compressive portions 360 are aligned with, and apply a clamping force to, overlapping U-shaped arm 354 and retroflexed arm 357 of the first and second rims. It will of course be understood that an overtube in accordance with the principles of the present invention couple alternatively be formed using Grecian links 350 and either of the clamping systems described with respect to FIGS. 32 and 33.

Figure 36:
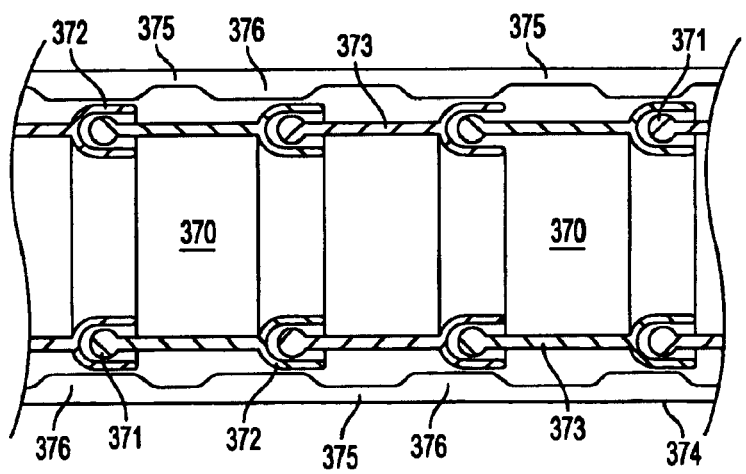
FIG. 36 is a side-sectional view of another alternative embodiment of the present invention comprising a series of links that form coacting joints.

Referring now to FIG. 36, yet another alternative embodiment of an overtube suitable for use in the present invention is described. This embodiment comprises joint links 370 that include ball 371 and socket 372 disposed at longitudinally opposing ends of flexible body 373. When adjacent joint links 370 are engaged, ball 371 of one link is disposed within socket 372 of an adjacent link. When the overtube is flexed, ball 371 coacts with socket 372 to provide articulation of the overtube.

Joint links 370 are disposed within compressive sleeve 374, which includes first compressive portions 375 and second compressive portions 376. Compressive sleeve 374 is identical in structure and operation to that described in FIGS. 31A, 34A and 35, except that second compressive portions 376 are aligned with, and apply a clamping force to, socket 372 within which ball 371 of an adjacent link is disposed. It will of course be understood that an overtube in accordance with the principles of the present invention couple alternatively be formed using joint links 370 and either of the clamping systems described with respect to FIGS. 32 and 33.

Figure 37:
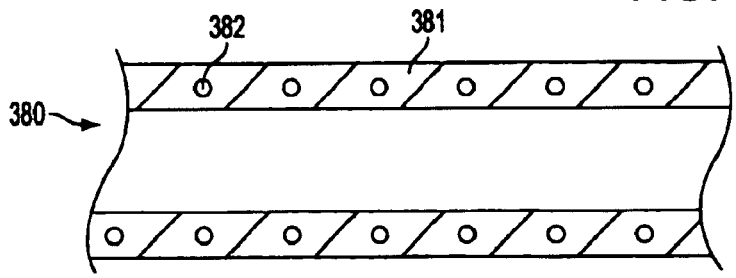
FIG. 37 is a side-sectional view of yet another alternative embodiment of an overtube having thermally regulated stiffness.

With respect to FIG. 37, a still further embodiment of an overtube suitable for use in the apparatus of the present invention is described. Overtube 380 comprises a heat-softenable polymer layer 381, (e.g., Carbothane®, a proprietary urethane-based polymer available from Thermedics Polymer Products, Woburn, Mass.), having wire 382 embedded within it. Wire 382 is coupled at the handle to an energy source, so that by passing an electric current through wire 382, sufficient resistive heating occurs to soften the polymer layer 381, rendering it sufficiently flexible to negotiate tortuous or unsupported anatomy. When electrical energy is not supplied to wire 382, no resistive heating of the wire or the polymer layer occurs, and the overtube instead cools and stiffens. Wire 382 serves the dual purpose of providing kink resistance and electric heating.

Still referring to FIG. 37, yet another alternative embodiment of an overtube suitable for use in the present invention comprises a soft elastomeric polymer layer 381 having a shape memory alloy wire 382 embedded within layer 381. In this embodiment, the shape memory alloy is selected to have a martensite transition temperature above body temperature. When wire 382 is heated to a temperature above body temperature, such as by passing an electric current through it, the wire transitions into the austenitic phase, and becomes stiffer, thereby shape locking the overtube. When application of the electric current ceases, wire 382 cools back into the martensitic phase, and renders the overtube flexible.

Figure 38A:
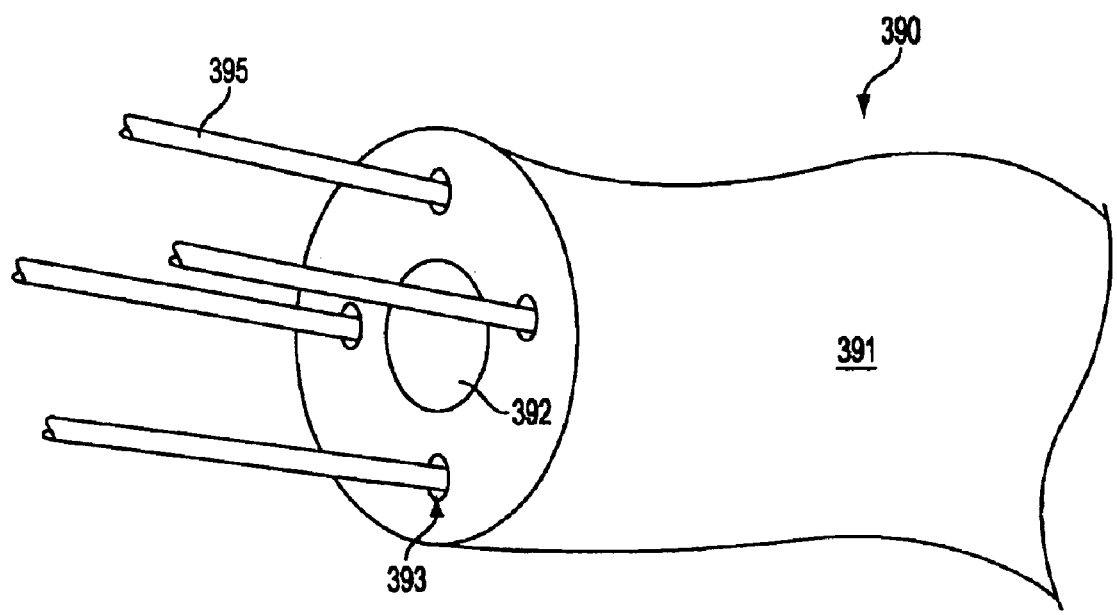
FIGS. 38A–38C are schematic views of yet another alternative embodiment of an overtube suitable for use with the present invention, in which the diameters of tension wire lumens extending through the overtube vary responsive to electrical energization.
Figures 38B, 38C:
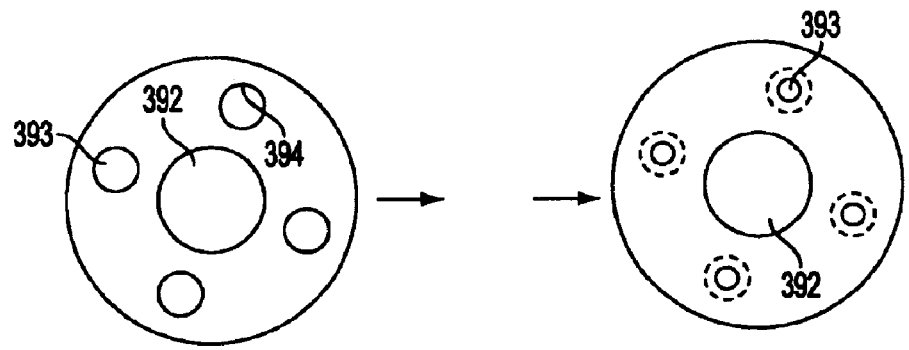

Referring now to FIGS. 38A–38C, an additional alternative embodiment of an overtube suitable for use with the present invention is described. Overtube 390 comprises elongate body 391 having central lumen 392 that accommodates colonoscope 10, and wire lumens 393 that are defined by cylindrical wire lumen surfaces 394. Within each wire lumen 393 is disposed wire 395 that extends the length of the elongate body. Elongate body 391 is made from an electroactive polymer known in the art that permits wire lumens 393 to vary in diameter responsive to electrical energization.

In particular, when an electrical current is passed through elongate body 391, the diameter of each wire lumen 393 decreases so that the wire lumens clamp around respective wires 395. Preferably, both wires 395 and wire lumen surfaces 394 are textured to enhance friction therebetween. This prevents further relative movement between elongate body 391 and wires 395, and stiffens overtube 390. When application of the electrical current ceases, wire lumens 393 increase in diameter to release wires 395 so that elongate body 391 may shift relative to wires 395. This in turn renders overtube 390 sufficiently flexible to negotiate a tortuous path through the colon.

Figure 39:
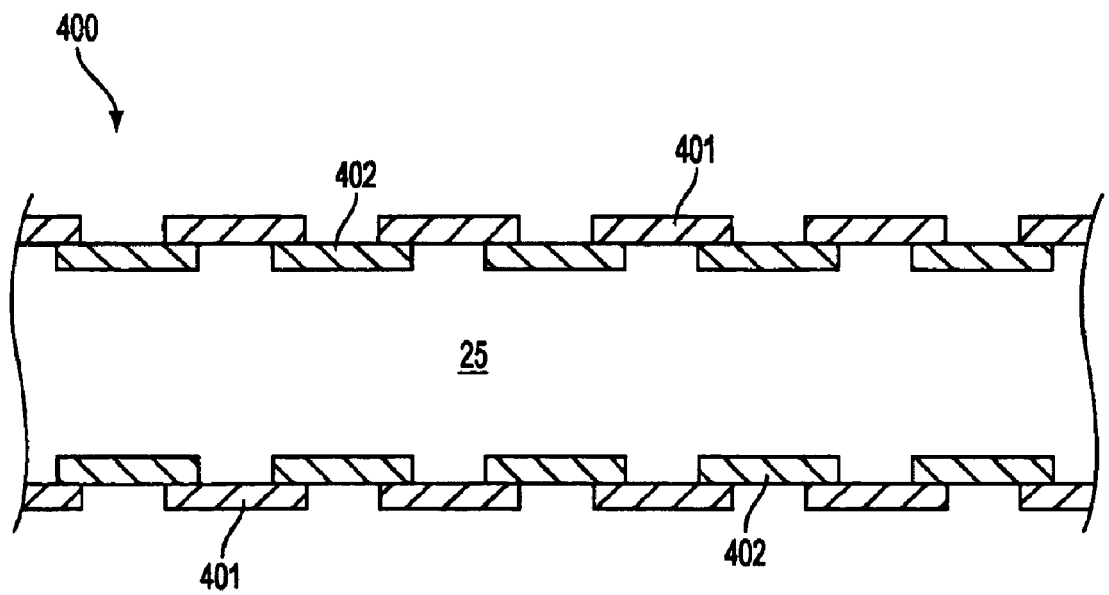
FIG. 39 is a side-sectional view of still another alternative embodiment of an overtube having a series of electrically activated links disposed in an overlapping fashion around a series of rigid links.

With respect to FIG. 39, yet another alternative embodiment of the overtube is described. Overtube 400 incorporates multiplicity of variable diameter links 401 disposed in overlapping fashion surrounding multiplicity of rigid links 402, that provide structural integrity to the overtube. Each link comprises a central bore that defines lumen 25 of the overtube, and accommodates a standard commercially available colonoscope. Variable diameter links 401 preferably are manufactured from an electroactive polymer or a shape memory alloy that contract in diameter when energized. When variable diameter links 401 are electrically activated, the variable diameter links tighten about rigid links 402 to transition overtube 400 into a shape-locked state. When the variable diameter links are electrically deactivated, the variable diameter links sufficiently soften to return overtube 400 back to the flexible state.

In a preferred embodiment, variable diameter links 401 and rigid links 402 are formed from respective strips of material that are helically wound in an overlapping fashion to form overtube 400. Alternatively, each link may be individually formed and disposed in an overlapping fashion.

Figures 40A, 40B:
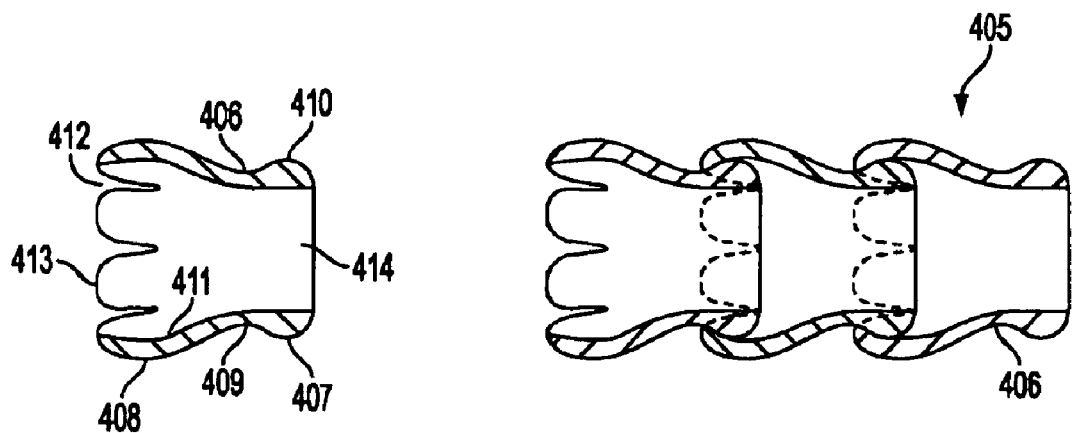
FIGS. 40A and 40B are side-sectional views of, respectively, an electrically activated nestable link and a plurality of the electrically activated nestable link of FIG. 40A nested together to form an overtube suitable for use with the apparatus of the present invention.

In FIGS. 40A–40B, still another alternative embodiment of an overtube suitable for use with the apparatus of the present invention is illustrated schematically. Overtube 405 comprises multiplicity of nestable hourglass elements 406 that preferably are manufactured from an electroactive polymer or a shape memory alloy, and each have bulbous distal and proximal portions 407 and 408 connected by neck 409. The diameter of neck 409 is smaller than the maximum diameter of distal portion 407, which in turn is less than the maximum diameter of proximal portion 408. The distal portion of external surface 410 of each hourglass element 406 is contoured to coact with the proximal portion of internal surface 411 of a distally adjacent hourglass element. Accordingly, when a multiplicity of hourglass elements are nested together to form overtube 405, adjacent elements 406 may move relative to each other when the overtube is in the flexible state.

To reduce friction between adjacent elements during relative movement therebetween, proximal portions 408 include plurality of slits 412 disposed contiguous with proximal edge 413. Slits 412 also facilitate contraction of proximal portion 408 of each element around distal portion 407 of an adjacent element. Each hourglass element 406 also has central bore 414 that accommodates colonoscope 10 (see FIG. 1).

When an electrical current is applied to multiplicity of nestable hourglass elements 406, proximal portion 408 of each element contracts in diameter around distal portion 407 of an adjacent element. The compressive clamping force thereapplied prevents relative movement between adjacent elements, thereby shape-locking the overtube. When the nestable elements are de-energized, proximal portions 408 sufficiently relax to permit relative movement between adjacent nestable elements 406, and thus permit overtube 405 to negotiate tortuous curves. For purposes of illustration, it should be understood that the figures of the present application may not depict an electrolytic medium, electrodes, and insulated wires that are coupled to and facilitate ionization, and thus contraction, of the electroactive polymers described herein.

Figure 41:
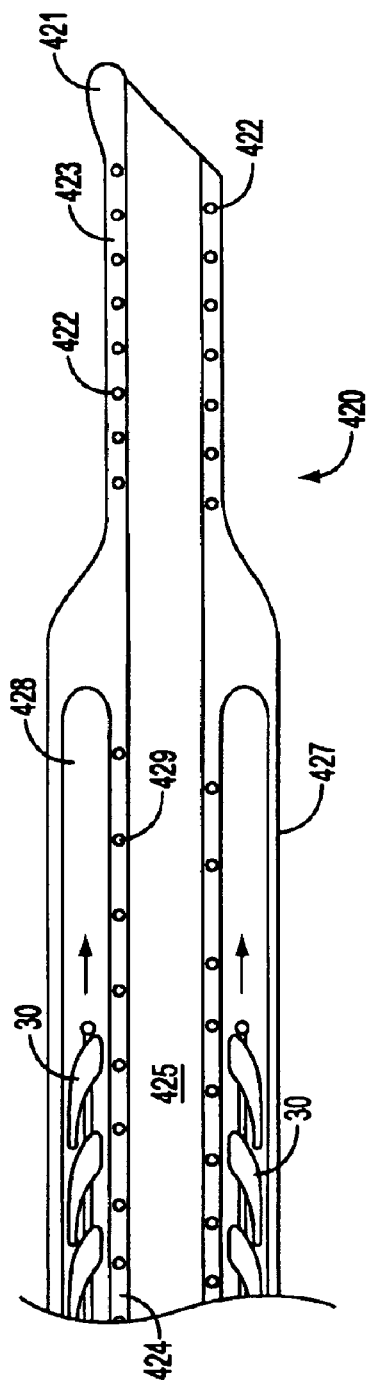
FIG. 41 is a side-sectional view of a disposable sheath for use with the overtube of the present invention.

In accordance with another aspect of the present invention, the overtube of the present invention may be provided with disposable sheath 420 that may extend the length of overtube 22 and be removed therefrom. Like the sheath described hereinabove with respect to FIG. 4, sheath 420 of FIG. 41 also incorporates distally-disposed atraumatic tip 421 and flexible, kink-resistant coil 422 encapsulated in flexible layer 423. At its proximal end, layer 423 joins or is integrally formed with lubricious liner 424 defining lumen 425, and flexible elastomeric skin 427. Liner 424 may incorporate optional flexible, kink-resistant coil 429, be made of a thin, flexible material, and/or have a hydrophilic coating thereon, similar to that described in reference to FIG. 4. Between liner 424 and skin 427 is disposed annular chamber 428 within which nestable elements 30 may be inserted. Sheath 420 is configured to slide onto and be removed from a column of nestable elements 30 so that the sheath may be discarded after a single use, while the nestable elements and handle may be sterilized and reused. Advantageously, substantial cost reductions may be realized.

Figure 42:
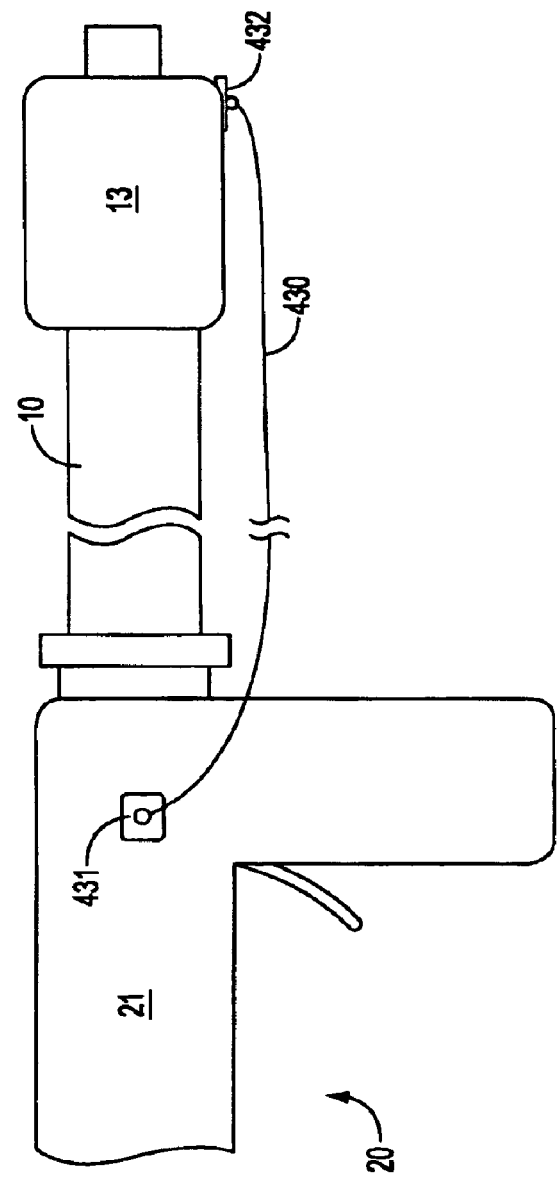
FIG. 42 is a schematic side view of a strap that couples the apparatus of the present invention to a colonoscope.

Pursuant to another aspect of the present invention, apparatus 20 further may be provided with a device to secure colonoscope 10 to apparatus 20 prior to insertion of apparatus 20 and colonoscope 10 into the patient. FIG. 42 depicts strap 430 that may be secured distally to handle 21 of apparatus 20 and proximally to proximal portion 13 of colonoscope 10. Strap 430 preferably has a length that prevents colonoscope 10 from decoupling from apparatus 20 after the colonoscope is placed within the overtube. Illustratively, strap 430 may be made of ductile wire or Velcro. If strap 430 is made of ductile wire, the strap may be secured to anchors 431 and 432 respectively disposed on handle 21 and colonoscope 10. Anchor 432 may be integral with, or comprise an adhesive suitable for application to colonoscope 10.

It will be obvious to one of ordinary skill in the art that, while the above description has emphasized use of apparatus 20 in the lower gastro-intestinal tract, and in particular, in performing colonoscopy, the apparatus of the present invention also may be used in the upper gastro-intestinal tract, and in laparoscopic procedures as a variable rigidity trocar through which a steerable laparoscopic endoscope or tool may be advanced. Apparatus 20 also may be scaled down in size for use in endo-urological procedures. For example, a miniaturized overtube may be advanced, along with a steerable nephrescope, through a patient's ureter into a kidney for access to the kidney's lower pole.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. Apparatus for advancing a first diagnostic or therapeutic instrument into a hollow body organ of unsupported anatomy, the apparatus comprising:
   a handle;
   an overtube coupled to the handle, the overtube having proximal and distal ends, an exterior surface, and an interior surface that defines a lumen extending between the proximal and distal ends to permit passage of the first diagnostic or therapeutic instrument; and
   a disposable sheath having a first portion that extends through the lumen to provide a barrier between the interior surface and the first diagnostic or therapeutic instrument and a second portion that extends over the exterior surface.

2. The apparatus of claim 1, wherein the disposable sheath comprises a hydrophilic material.

3. The apparatus of claim 1, wherein the disposable sheath comprises a non-kinking coil.

4. The apparatus of claim 1, wherein the first portion comprises a thin, flexible material.

5. The apparatus of claim 1, wherein the overtube comprises a plurality of nestable links that each has a lateral wall.

6. The apparatus of claim 5, wherein the plurality of nestable links are made from a material selected from the group consisting of polymers, metals, and combinations thereof.

7. The apparatus of claim 6, wherein the polymer is filled with glass fiber, carbon fiber, or combinations thereof.

8. The apparatus of claim 7, wherein the polymer is polyurethane.

9. The apparatus of claim 5, wherein each one of the plurality of nestable links comprises a distal surface and a proximal surface.

10. The apparatus of claim 9, wherein the distal surface is macroscopically textured, and the proximal surface comprises teeth configured to engage the distal surface.

11. The apparatus of claim 10, wherein each one of the plurality of nestable links further comprises one or more springs that prevent coaction between the distal and proximal surfaces of adjacent ones of the plurality of nestable links, absent an externally applied force.

12. The apparatus of claim 10, further comprising a plurality of elastomeric discs, wherein each one of the plurality of elastomeric discs is disposed between adjacent ones of the plurality of nestable links.

13. The apparatus of claim 9, wherein each one of the plurality of nestable links further comprises a proximal edge and a band circumferentially disposed around the distal surface adjacent to the proximal edge.

14. The apparatus of claim 9, wherein a radius of curvature of the proximal surface closely approximates a radius of curvature of the distal surface.

15. The apparatus of claim 9, wherein a coefficient of static friction between the distal and proximal surfaces are within a range of about 0.2 to 1.4, inclusive.

16. The apparatus of claim 5, further comprising:
a plurality of tension wire bores extending through the lateral wall of each one of the plurality of nestable links; and
at least one tension wire translatably disposed through one or more of the plurality of tension wire bores.

17. The apparatus of claim 16, wherein the at least one tension wire has a first diameter and each one of the plurality of tension wire bores has a second diameter, and the ratio of the first diameter to the second diameter is in a range of approximately ½ to ⅔.

18. The apparatus of claim 5, wherein each one of the plurality of nestable links comprises an integral lubricious liner.

19. The apparatus of claim 5, wherein the overtube further comprises a flexible state that facilitates insertion of the overtube into a hollow body organ, and a rigid state wherein the overtube resists bending forces exerted on the interior surface during insertion or withdrawal of the first diagnostic or therapeutic instrument though the lumen.

20. The apparatus of claim 19, further comprising a tensioning mechanism selectively operable to transition the overtube between the flexible and rigid states.

21. The apparatus of claim 20, wherein the tensioning mechanism has a fail-safe mode that reduces the risk of undesired reconfiguration of the overtube in the event of tensioning mechanism failure.

22. The apparatus of claim 21, wherein the tensioning mechanism comprises a plurality of tension wires that threads the plurality of nested links together.

23. The apparatus of claim 22, wherein the tensioning mechanism is configured so that tension within each one of the plurality of tension wires is dependent on tension within the remaining plurality of tension wires.

24. The apparatus of claim 22, wherein the tensioning mechanism comprises a pulley manifold.

25. The apparatus of claim 24, wherein the pulley manifold further comprises a plurality of grooves within which the plurality of wires are slidably disposed.

26. The apparatus of claim 25, wherein the plurality of grooves are disposed on a lateral surface of the pulley manifold.

27. The apparatus of claim 25, wherein the plurality of grooves are disposed on a proximal surface of the pulley manifold.

28. The apparatus of claim 24, wherein the pulley manifold is affixed within the handle.

29. The apparatus of claim 22, wherein the plurality of tension wires comprises at least one length of wire.

30. The apparatus of claim 22, wherein the plurality of tension wires comprises a shape memory material.

31. The apparatus of claim 22, wherein the plurality of tension wires comprises a superelastic material.

32. The apparatus of claim 20, wherein the tensioning mechanism further comprises a piston.

33. The apparatus of claim 20, wherein the tensioning mechanism comprises a spring.

34. The apparatus of claim 20, wherein the tensioning mechanism comprises a damper.

35. The apparatus of claim 20, wherein the tensioning mechanism is selectively operable to transition the overtube between the flexible and rigid states without substantial proximal movement of the distal end of the overtube.

36. The apparatus of claim 35, wherein the tensioning mechanism is configured to apply a distally-directed clamping load to the plurality of nestable links.

37. The apparatus of claim 20, wherein the tensioning mechanism further comprises a plurality of nestable bridge links interposed between a predetermined number of the plurality of nestable links, and a plurality of ribbons, wherein each one of the plurality of ribbons is coupled to adjacent ones of the plurality of nestable bridge links.

38. The apparatus of claim 37, wherein the plurality of ribbons comprises a shape memory material.

39. The apparatus of claim 20, wherein the tensioning mechanism is configured to transition the overtube from the flexible state to the rigid state with a single actuation of the actuator.

40. The apparatus of claim 20, wherein the tensioning mechanism is configured to transition the overtube between the flexible and rigid states with successive actuations of the actuator.

41. The apparatus of claim 5, wherein the plurality of nestable links comprises a shape memory material.

42. The apparatus of claim 5, wherein the overtube increases in axial length by less than or equal to approximately 0.31 inch when one of the plurality of nestable links is nested within another one of the plurality of nestable links.

43. The apparatus of claim 1, wherein the overtube comprises an elongate body made from the shape memory material, at least one wire, and a plurality of wire lumens disposed parallel to a longitudinal axis of the elongate body, the at least one wire disposed through one or more of the plurality of wire lumens.

44. The apparatus of claim 43, wherein one or more of the plurality of wire lumens are configured to grippingly engage the at least one wire when the elongate body is energized.

45. The apparatus of claim 1, wherein the overtube comprises a plurality of shape memory links disposed in an overlapping fashion around a plurality of rigid links.

46. The apparatus of claim 1, wherein the handle further comprises an extension suitable for insertion into the hollow body organ.

47. The apparatus of claim 1, wherein the handle has a length less than or equal to approximately 5 inches.

48. The apparatus of claim 1, wherein the handle comprises an indicator that provides information about the rigidity of the overtube.

49. The apparatus of claim 1, wherein a thickness of the overtube is less than or equal to approximately 1 mm.

50. The apparatus of claim 1, further comprising a strap configured to releasably couple the handle of the apparatus to a proximal end of the first diagnostic or therapeutic instrument.

51. The apparatus of claim 1, wherein the handle further comprises a shield that prevents a proximal portion of the handle from being inadvertently inserted into the hollow body organ.

* * * * *